US012605672B2

(12) United States Patent
Foody et al.

(10) Patent No.: US 12,605,672 B2
(45) Date of Patent: Apr. 21, 2026

(54) METHOD AND SYSTEM FOR UPGRADING BIOGAS USING PSA

(71) Applicant: Iogen Corporation, Ottawa (CA)

(72) Inventors: Brian Foody, Ottawa (CA); Jeffrey S. Tolan, Ottawa (CA); John Dechman, Ottawa (CA)

(73) Assignee: Iogen Corporation, Ottawa (CA)

( * ) Notice: Subject to any disclaimer, the term of this patent is extended or adjusted under 35 U.S.C. 154(b) by 222 days.

(21) Appl. No.: 18/695,785

(22) PCT Filed: Sep. 21, 2022

(86) PCT No.: PCT/CA2022/051404
§ 371 (c)(1),
(2) Date: Mar. 26, 2024

(87) PCT Pub. No.: WO2023/049994
PCT Pub. Date: Apr. 6, 2023

(65) Prior Publication Data
US 2025/0128201 A1     Apr. 24, 2025

Related U.S. Application Data

(60) Provisional application No. 63/261,764, filed on Sep. 28, 2021.

(51) Int. Cl.
B01D 53/047     (2006.01)
B01D 53/14      (2006.01)
(Continued)

(52) U.S. Cl.
CPC ....... B01D 53/047 (2013.01); B01D 53/1475 (2013.01); B01D 53/44 (2013.01);
(Continued)

(58) Field of Classification Search
CPC .. B01D 53/047; B01D 53/1475; B01D 53/44; B01D 2256/245; B01D 2257/102;
(Continued)

(56) References Cited

U.S. PATENT DOCUMENTS 2,638,999 A     5/1953  Berg
2,656,010 A    10/1953  Thodos
(Continued)

FOREIGN PATENT DOCUMENTS

EP     1 042 065    3/2003
GB     1 059 974    2/1967
(Continued)

OTHER PUBLICATIONS

Bauer et al., "Biogas Upgrading—Review of Commercial Technologies", SGC Rapport 2013:270, 2013, in 84 pages.
(Continued)

*Primary Examiner* — Ellen M McAvoy
(74) *Attorney, Agent, or Firm* — Knobbe, Martens, Olson & Bear, LLP

(57)     ABSTRACT

A method for upgrading biogas comprising methane and nitrogen, where the biogas is provided in at least one pressurized vessel at a pressure of at least 65 atm (6586 kPa). The method includes a pressure swing adsorption (PSA) cycle having a feed phase, where biogas is fed into a first adsorbent bed when the inlet end is open and the outlet end is closed, followed by a first depressurization phase, where a gas enriched in methane is withdrawn through the outlet end with the inlet end being closed. This gas enriched in methane can be pipeline quality and at pipeline pressures. A methane recovery phase is provided, which can improve methane recovery, wherein gas is withdrawn and the pressure drops to one or more lower values, and where this gas
(Continued)

can be recycled for use in the feed phase, used in a regeneration phase, and/or fed to a second bed.

21 Claims, 17 Drawing Sheets

(51) Int. Cl.
| | |
|---|---|
| *B01D 53/44* | (2006.01) |
| *C07C 7/12* | (2006.01) |
| *C10L 3/00* | (2006.01) |

(52) U.S. Cl.
CPC .................................... *C07C 7/12* (2013.01); *C10L 3/00* (2013.01); *B01D 2256/245* (2013.01); *B01D 2257/102* (2013.01); *B01D 2257/304* (2013.01); *B01D 2257/504* (2013.01); *B01D 2258/05* (2013.01); *B01D 2259/4002* (2013.01); *B01D 2259/40032* (2013.01); *B01D 2259/40052* (2013.01); *B01D 2259/40062* (2013.01); *B01D 2259/40064* (2013.01); *B01D 2259/402* (2013.01)

(58) Field of Classification Search
CPC ........ B01D 2257/304; B01D 2257/504; B01D 2258/05; C07C 7/12; C10L 3/00
See application file for complete search history.

(56) References Cited

U.S. PATENT DOCUMENTS

| | | | |
|---|---|---|---|
| 2,843,219 A | 7/1958 | Habgood | |
| 3,738,087 A | 6/1973 | McCombs | |
| 4,013,429 A | 3/1977 | Sircar et al. | |
| 4,194,891 A | 3/1980 | Earls et al. | |
| 4,690,695 A | 9/1987 | Doshi | |
| 4,770,676 A | 9/1988 | Sircar et al. | |
| 4,813,980 A | 3/1989 | Sircar | |
| 5,174,796 A | 12/1992 | Davis et al. | |
| 5,989,316 A | 11/1999 | Kuznicki et al. | |
| 6,096,115 A | 8/2000 | Kleinberg et al. | |
| 6,102,985 A | 8/2000 | Naheiri et al. | |
| 6,290,751 B1 | 9/2001 | Ragil et al. | |
| 6,315,817 B1 | 11/2001 | Butwell et al. | |
| 6,428,607 B1 | 8/2002 | Xu et al. | |
| 6,444,012 B1 | 9/2002 | Dolan et al. | |
| 6,497,750 B2 | 12/2002 | Butwell et al. | |
| 6,585,804 B2 | 7/2003 | Kleinberg et al. | |
| 7,179,324 B2 | 2/2007 | Baksh et al. | |
| 7,674,319 B2 | 3/2010 | Lomax, Jr. et al. | |
| 7,731,779 B2 | 6/2010 | Palumbo | |
| 7,959,720 B2 | 6/2011 | Deckman et al. | |
| 8,192,527 B2 | 6/2012 | Pirngruber et al. | |
| 8,211,211 B1 | 7/2012 | Knaebel | |
| 8,221,524 B2 | 7/2012 | Mitariten | |
| 9,034,079 B2 | 5/2015 | Deckman et al. | |
| 9,944,575 B2 | 4/2018 | Kawashima et al. | |
| 10,760,024 B2 | 9/2020 | Foody et al. | |
| 12,515,167 B2 * | 1/2026 | Foody .................. | B01D 53/226 |
| 2006/0191410 A1 | 8/2006 | Dolan et al. | |
| 2015/0101671 A1 | 4/2015 | Paget et al. | |
| 2017/0056815 A1 * | 3/2017 | Nagavarapu ....... | B01D 53/0462 |
| 2019/0134556 A1 * | 5/2019 | Ho ...................... | B01D 53/047 |
| 2021/0008487 A1 | 1/2021 | Stuckert et al. | |
| 2021/0016218 A1 | 1/2021 | Stuckert et al. | |
| 2021/0060477 A1 * | 3/2021 | Thompson ........... | B01D 53/053 |
| 2021/0077942 A1 | 3/2021 | Stuckert et al. | |
| 2021/0229027 A1 | 7/2021 | Da Silva Barcia et al. | |
| 2024/0189760 A1 * | 6/2024 | Iuhas ...................... | C10L 3/106 |
| 2025/0001351 A1 * | 1/2025 | Foody ...................... | C07C 7/12 |

FOREIGN PATENT DOCUMENTS

| | | |
|---|---|---|
| WO | WO 2008/072215 | 6/2008 |
| WO | WO 2011/139894 | 11/2011 |
| WO | WO 2019/185315 | 10/2019 |
| WO | WO 2019/191421 | 10/2019 |
| WO | WO 2019/239381 | 12/2019 |
| WO | WO 2020/234901 | 11/2020 |
| WO | WO 2022/087755 | 5/2022 |
| WO | WO 2023/049993 | 4/2023 |
| WO | WO 2023/049994 | 4/2023 |

OTHER PUBLICATIONS

Bhadra, Shubhra Jyoti, "Methane-Nitrogen Separation by Pressure Swing Adsorption", Master's Thesis, National University of Singapore, 2007, in 171 pages.

Bhadra et al., "Separation of Methane—Nitrogen Mixture by Pressure Swing Adsorption for Natural gas Upgrading", Industrial & Engineering Chemistry Research, 2011, vol. 50, pp. 14030-14045.

Defrate et al., "Optimum Design of Ejectors using Digital Computers", Chemical Engineering Progress Symposium Series, Computer Techniques, 1959, vol. 55, pp. 43-51.

Dhoke et al., "Review on Reactor Configurations for Adsorption-based CO2 Capture", Industrial & Engineering Chemistry Research, Mar. 2021, vol. 60, pp. 3779-3798.

Effendy et al., "Optimization of a Pressure Swing Adsorption Process for Nitrogen Rejection from Natural Gas", Industrial & Engineering Chemistry Research, Apr. 2017, vol. 56, pp. 5417-5431.

Grande, Carlos A., "Chapter 3—Biogas Upgrading by Pressure Swing Adsorption", Biofuel's Engineering Process Technology, InTech, Aug. 2011, in 23 pages.

Gulbalkan et al., "Assessing CH4/N2 Separation Potential of MOFs, COFs, IL/MOF, MOF/Polymer, and COF/Polymer Composites", Chemical Engineering Journal, 2022, vol. 428, 131239, in 10 pages.

Keenan et al., "An Investigation of Ejector Design by Analysis and Experiment", Journal of Applied Mechanics, Sep. 1950, pp. 299-309.

Lokhandwala et al., "Nitrogen Removal from Natural Gas—Phase II Draft Final Report", Membrane Technology and Research, Inc., 1999, in 50 pages.

Mota et al., "Synchronous and Asynchronous SMB Processes for Gas Separation", American Institute of Chemical Engineers, May 2007, vol. 53, No. 5, pp. 1192-1203.

Quian et al., "An Improved Vacuum Pressure Swing Adsorption Process with the Simulated Moving Bed Operation Mode for CH4/N2 Separation to Produce High-Purity Methane", Chemical Engineering Journal, 2021, vol. 419, 129657, in 14 pages.

Rufford et al., "The removal of CO2 and N2 from natural gas: A review of conventional and emerging process technologies", Journal of Petroleum Science and Engineering, vol. 94-95, Sep. 2012, pp. 123-154.

International Search Report and Written Opinion in PCT Application No. PCT/CA2022/051403, dated Dec. 21, 2022.

International Search Report and Written Opinion in PCT Application No. PCT/CA2022/051404, dated Dec. 22, 2022.

* cited by examiner

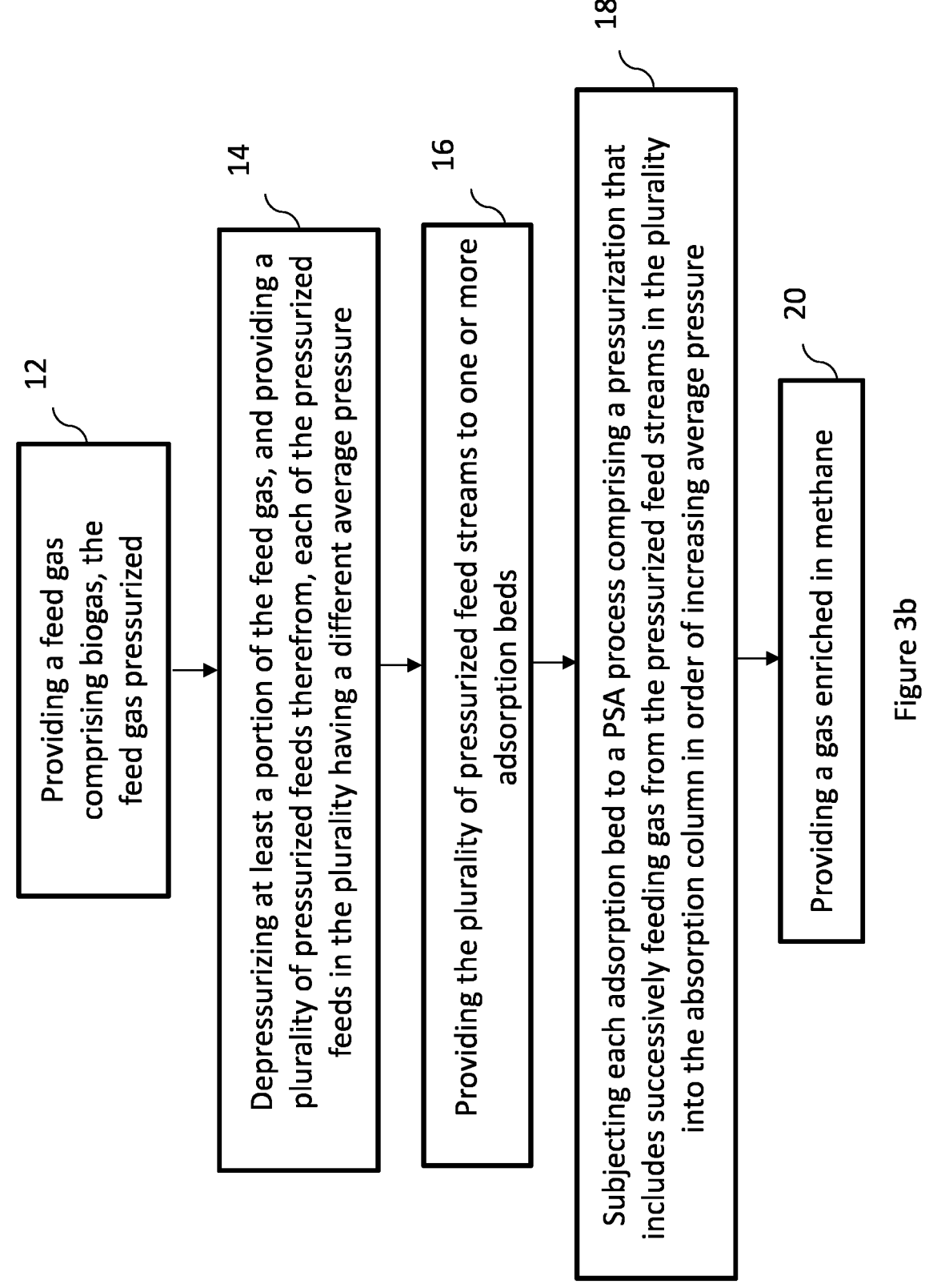

12

Providing a feed gas comprising biogas, the feed gas pressurized

14

Depressurizing at least a portion of the feed gas, and providing a plurality of pressurized feeds therefrom, each of the pressurized feeds in the plurality having a different average pressure

16

Providing the plurality of pressurized feed streams to one or more adsorption beds

18

Subjecting each adsorption bed to a PSA process comprising a pressurization that includes successively feeding gas from the pressurized feed streams in the plurality into the absorption column in order of increasing average pressure

20

Providing a gas enriched in methane

Figure 3b

METHOD AND SYSTEM FOR UPGRADING BIOGAS USING PSA

TECHNICAL FIELD

The present disclosure relates to a method and system for upgrading biogas, and in particular, relates to a method and system for upgrading biogas that includes pressure swing adsorption (PSA).

BACKGROUND

Biogas, which is a mixture of several gases, is typically produced by the breakdown of organic matter by microorganisms under anaerobic or low oxygen conditions. In particular, it can be produced by the anaerobic digestion or fermentation of organic matter (e.g., manure, sewage sludge, municipal solid waste, biodegradable waste, biodegradable feedstock, etc.).

Biogas collected at its source (e.g., a landfill or anaerobic digester) is typically referred to as raw biogas. Without being limiting, raw biogas may have a methane ($CH_4$) content between about 35% and about 75% (e.g., average about 60%), a carbon dioxide ($CO_2$) content between about 15% and about 65% (e.g., average about 35%), a nitrogen ($N_2$) content in the range of about 0-20%, an oxygen ($O_2$) content in the range of about 0-5%, and a hydrogen sulfide ($H_2S$) content of about 0 to 4000 ppm. Raw biogas, which is often saturated with water ($H_2O$), may also contain ammonia ($NH_3$), hydrogen ($H_2$), volatile organic compounds (VOCs), and/or siloxanes, depending on the source and/or organic matter from which it is derived.

Raw biogas can be treated to produce an upgraded gas that is primarily $CH_4$ (e.g., >95% $CH_4$). If of sufficient purity, the upgraded biogas may be used interchangeably with natural gas and may be referred to as renewable natural gas (RNG). As a result of the various non-methane components, biogas upgrading often requires multiple steps, each of which may rely on one or more technologies. For example, the first steps of biogas upgrading may include hydrogen sulfide removal (e.g., activated carbon filter, iron sponge, biotrickling filter, etc.), water removal (e.g., drying via refrigeration techniques or desiccants), and/or volatile organic compound (VOC) removal (e.g., adsorption). Carbon dioxide may then be removed using membrane separation, adsorption, absorption, and/or cryogenic processes designed to separate $CH_4$ and $CO_2$. A separate nitrogen removal, if required, is often conducted after $CO_2$ removal. Such nitrogen removal, which can be referred to as nitrogen rejection, may be conducted using membrane separation, adsorption, absorption, and/or cryogenic processes designed to separate $CH_4$ and $N_2$.

In terms of biogas upgrading, there have been many advances that facilitate $CO_2$ removal from biogas. However, relative to $CH_4/CO_2$ separations, $CH_4/N_2$ separations may be more challenging. Accordingly, the selection of suitable technology for biogas upgrading wherein $N_2$ is removed from the biogas after a $CO_2$ removal can be difficult. While cryogenic $CH_4/N_2$ separations can be effective, this technology is often limited to relatively large scale plants due to expensive installations and/or high energy-consuming operation. Pressure swing adsorption (PSA) also has been used for $CH_4/N_2$ separations. However, while PSA may have the potential to efficiently reject nitrogen across various scales of flow rate, its use may be limited by economic challenges and/or the trade-off between methane purity and methane recovery.

SUMMARY

The instant disclosure relates to a method and/or system wherein biogas provided in one or more pressurized vessels is upgraded using PSA, and wherein a relatively high pressure of the pressurized biogas is used to improve the PSA process (e.g., reduce economic challenges and/or the trade-off between methane purity and methane recovery). The instant disclosure is particularly useful for biogas upgrading wherein $CH_4$ and $N_2$ are separated.

In accordance with one aspect of the instant invention there is provided a method of upgrading biogas comprising methane and nitrogen, the method comprising: (i) providing the biogas in at least one pressurized vessel, the biogas provided at least initially at a pressure of at least 65 atm (6586 kPa); (ii) treating at least a portion of the biogas in a pressure swing adsorption (PSA) process, the PSA process comprising feeding the portion of the biogas into a first adsorbent bed disposed in series with a second adsorbent bed, the first adsorbent bed having an inlet end and an outlet end, the first adsorbent bed comprising an adsorbent selective for nitrogen over methane and subjected to a first PSA cycle, the first PSA cycle comprising: (a) a feed phase, wherein the portion of the biogas is fed into the first adsorbent bed when the inlet end is open and the outlet end is closed, thereby pressurizing the first adsorbent bed to a first pressure and preferentially adsorbing the nitrogen over the methane, the first pressure being at least 40 atm (4053 kPa); (b) a first depressurization phase, wherein the inlet end is closed, the outlet end is open, and a gas enriched in methane is withdrawn through the outlet end as the pressure of the first adsorbent bed falls to a second pressure, the second pressure lower than the first pressure, at least a portion of the gas enriched in methane provided as product gas; (c) a methane recovery phase, wherein gas is withdrawn from the inlet end, outlet end, or a combination thereof, as the pressure of the first adsorbent bed falls to a third pressure, the third pressure being lower than the second pressure, at least a portion of the gas withdrawn from the first adsorbent bed during the methane recovery phase recycled for use in the feed phase, used in a regeneration phase, fed to the second bed, or any combination thereof; and, (d) optionally, the regeneration phase, wherein the first adsorbent bed is depressurized to 1 atm (101 kPa) or lower, subjected to a purge step, or a combination thereof.

In accordance with one aspect of the instant invention there is provided a method of upgrading biogas comprising methane and nitrogen, the method comprising: (i) providing the biogas in at least one pressurized vessel, the biogas provided at least initially at a pressure of at least 65 atm (6586 kPa); (ii) treating at least a portion of the biogas in a pressure swing adsorption (PSA) process, the PSA process comprising feeding the portion of the biogas into a first adsorbent bed disposed in series with a second adsorbent bed, the first adsorbent bed having an inlet end and an outlet end, the first adsorbent bed comprising an adsorbent selective for nitrogen over methane and subjected to a first PSA cycle, the first PSA cycle comprising: (a) a feed phase, wherein the first portion of the biogas is fed into the first adsorbent bed when the inlet end is open and the outlet end is closed, thereby pressurizing the first adsorbent bed to a first pressure and preferentially adsorbing the nitrogen over the methane, the first pressure at least 40 atm (4053 kPa); (b) a first depressurization phase, wherein the inlet end is closed, the outlet end is open, and a first gas enriched in methane is withdrawn through the outlet end as the pressure of the first adsorbent bed falls to a second pressure, the second pressure at least 34 atm (3447 kPa) and lower than the first pressure, at least a portion of the first gas enriched in methane provided as product gas; (c) a second depressurization phase, wherein the inlet end is closed, the outlet end is open, and a second gas enriched in methane is withdrawn through the outlet end as the pressure of the first adsorbent bed falls to a third pressure, the third pressure lower than the second pressure, at least a portion of the second gas enriched in methane used within the PSA process; (d) a third depressurization phase, wherein gas is withdrawn from the inlet end, the outlet end, or a combination thereof, as the pressure of the first adsorbent bed falls to a fourth pressure, the fourth pressure lower than the third pressure, at least a portion of the withdrawn gas recycled for use in the feed phase; and (e) optionally, a regeneration phase, wherein the first adsorbent bed is depressurized to 1 atm (101 kPa) or lower, subjected to a purge step, or a combination thereof.

In accordance with one aspect of the instant invention there is provided a method of upgrading biogas comprising a pressure swing adsorption process, the pressure swing adsorption process comprising: (a) a feed step, the feed step comprising feeding the biogas into an adsorbent bed having an adsorbent selective for at least one non-methane component of the biogas, the adsorbent bed having an inlet end and an outlet end, the feeding comprising passing the biogas through a first valve near the inlet end while a second valve near the outlet end is closed, thereby pressurizing the adsorbent bed to a first pressure and preferentially adsorbing the at least one non-methane component; (b) a first depressurization step, the first depressurization step comprising closing the first valve, opening the second valve, and withdrawing a gas enriched in methane through the second valve as the pressure in the adsorbent bed falls to a second pressure, the second pressure lower than the first pressure; (c) a second depressurization, the second depressurization comprising opening the first valve and simultaneously withdrawing a first portion of the gas in the adsorbent bed through the first valve, and a second portion of the gas in the adsorbent bed through the second valve; and (d) regeneration, the regeneration comprising purging the adsorbent bed, heating the adsorbent bed, evacuating the adsorbent bed, or a combination thereof.

In accordance with one aspect of the instant invention there is provided a method of upgrading biogas comprising methane and nitrogen, the method comprising: (i) providing the biogas in at least one pressurized vessel, the biogas provided at least initially at a pressure of at least 65 atm (6586 kPa); (ii) treating at least a portion of the biogas in a pressure swing adsorption (PSA) process, the PSA process comprising feeding the portion of the biogas into an adsorbent bed, the adsorbent bed having an inlet end and an outlet end, the adsorbent bed comprising an adsorbent selective for nitrogen over methane and subjected to a PSA cycle, the PSA cycle comprising: a feed phase, wherein the portion of the biogas is fed into the adsorbent bed when the inlet end is open and the outlet end is closed, thereby pressurizing the adsorbent bed to a first pressure and preferentially adsorbing the nitrogen over the methane, the first pressure being at least 40 atm (4053 kPa); a first depressurization phase, wherein the inlet end is closed, the outlet end is open, and a gas enriched in methane is withdrawn through the outlet end as the pressure of the adsorbent bed falls to a second pressure, the second pressure lower than the first pressure, at least a portion of the gas enriched in methane provided as product gas; a methane recovery phase, wherein gas is withdrawn from the inlet end, outlet end, or a combination thereof, as the pressure of the adsorbent bed falls to a third pressure, the third pressure being lower than the second pressure, at least a portion of the gas withdrawn from the adsorbent bed during the methane recovery phase recycled for use in the feed phase, used in a regeneration phase, fed to another bed, or any combination thereof; and, optionally, the regeneration phase, wherein the adsorbent bed is depressurized to 1 atm (101 kPa) or lower, subjected to a purge step, or a combination thereof.

BRIEF DESCRIPTION OF THE DRAWINGS

FIG. 3*b* is a flow diagram of a method in accordance with another embodiment of the instant invention;

DETAILED DESCRIPTION

Adsorption refers to the spontaneous phenomenon of attraction that a molecule in a fluid phase (e.g., gas phase) experiences when close to the surface of a solid. In terms of gas separations, adsorption processes typically involve passing a gaseous mixture through one or more pressurized beds of adsorbent material such that some of the gas is trapped on the solid surface (i.e., is adsorbed). The higher the pressure, the more gas is adsorbed. If the pressure is sufficiently reduced, the adsorbed gas is typically released (i.e., is desorbed).

Pressure swing adsorption (PSA), which is a cyclic process, exploits this dependency on pressure by alternating between an adsorption phase wherein gas is adsorbed at high pressure and a desorption phase wherein gas is desorbed a relatively low pressure. Appropriate selection of the adsorbent material can result in one or more components of a gaseous mixture being preferentially adsorbed on the adsorbent material (e.g., based on molecular size, affinity for the adsorbent, and/or rates of diffusion in the pores of the adsorbent material). For purposes herein the one or more components of a gaseous mixture that are preferentially adsorbed are referred to as the "adsorbed species", whereas the other component(s) of the gaseous mixture are referred to as the "unadsorbed species." Choice of both the adsorbent material and the properties of the cycle (e.g., operating conditions and operating mode) can affect the separation of the adsorbed species from the unadsorbed species, and thus can affect product purity and/or product recovery.

Figure 1:
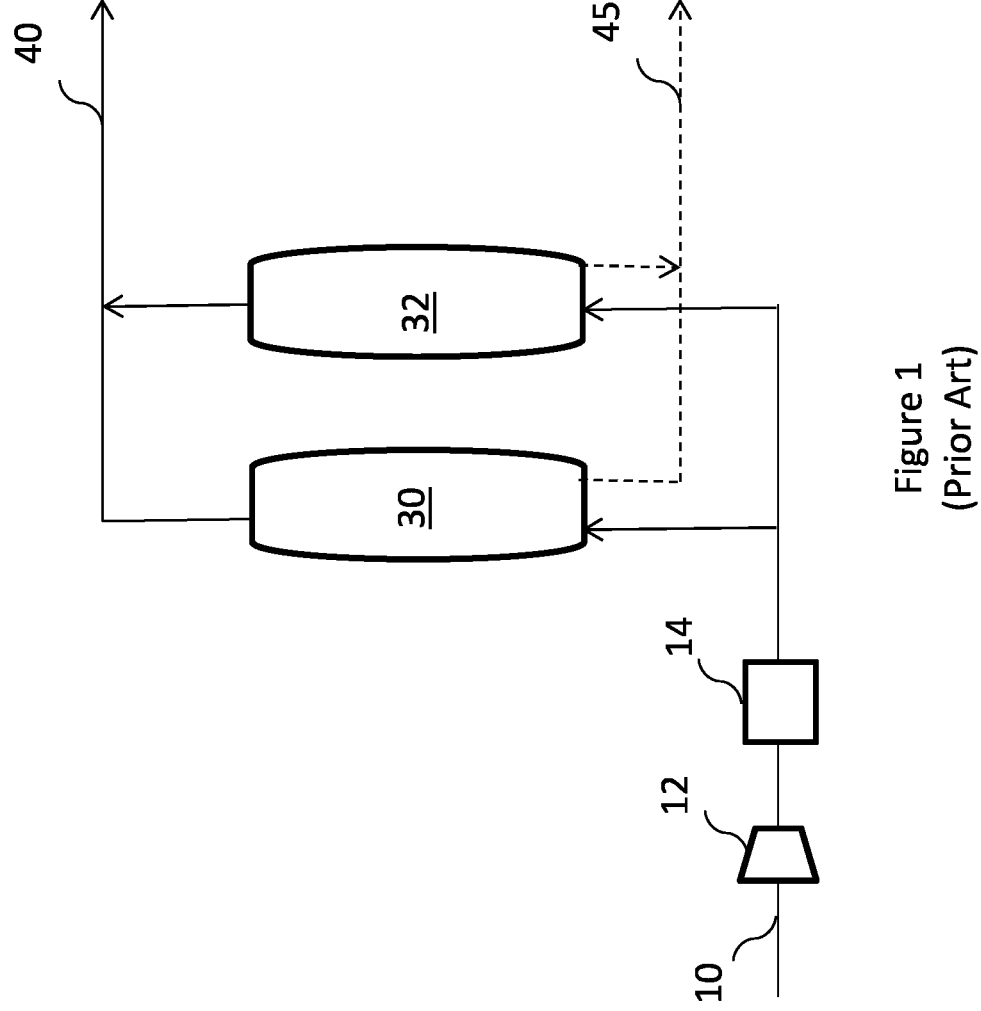
FIG. 1 is a schematic diagram showing a simplified biogas upgrading process.

For example, consider the simplified biogas upgrading process illustrated in FIG. 1. Raw biogas 10, which in this case predominately contains $CO_2$ and $CH_4$, is provided as feed for the PSA process. The biogas 10 is compressed 12 to an elevated pressure (e.g., 50-150 psig), is subjected to $H_2S$ removal 14, is dried (not shown), and is then fed through an inlet of an adsorbent bed 30. The adsorbent bed 30 is packed with an adsorbent that is selective for $CO_2$. As the biogas is passed over the pressurized adsorbent bed 30 the adsorbent material preferentially retains $CO_2$ over $CH_4$ so that a stream enriched in $CH_4$ can be withdrawn from the outlet at the opposite end of the adsorbent bed 30 and provided as product gas 40. When the adsorbent bed 30 is saturated with $CO_2$ (i.e., cannot adsorb more $CO_2$), and/or prior to significant breakthrough of $CO_2$ at the outlet of the adsorbent bed 30, the step of feeding the biogas to the adsorbent bed 30 is terminated and regeneration of the adsorbent bed 30 may begin. Regeneration can include depressurizing the adsorbent bed, purging the adsorbent bed, and/or evacuating the adsorbent bed (e.g., drawing a vacuum). The gas withdrawn from the adsorbent bed 30 during the desorption phase can be provided as off-gas 45. The off-gas may be disposed of, be further purified, and/or be used within the process. Providing at least two adsorbent beds allows one adsorbent bed (e.g., 30) to be in the adsorption phase, while another bed (e.g., 32) is in the desorption phase. Some factors that may affect the purity and/or recovery of the product gas 40 include the selectivity of the adsorbent material, whether breakthrough of the $CO_2$ occurs before the end of the adsorption phase, the amount of $CH_4$ retained within the adsorbent bed at the end of the adsorption phase and whether any steps are taken to recover this $CH_4$, the amount of $CH_4$ retained within the adsorbent bed at the end of depressurization, and/or the amount of $CO_2$ retained in the adsorbent bed at the end of the desorption phase. For example, at the end of the depressurization some $CH_4$ and/or $CO_2$ may be retained within the void space of the adsorbent bed.

In general, there is often a trade-off between product purity and product recovery for PSA processes. Various processes have been proposed to improve the purity and/or recovery of the product gases produced by PSA, many of which expand on the four-step configuration of early Skarstrom cycles. In Skarstrom-type cycles, the adsorption and desorption phases can be conducted over four steps, namely, 1) pressurization, 2) adsorption, 3) blowdown, and 4) purge. The pressurization step typically involves pressurizing the adsorbent bed 30 to an upper pressure (e.g., using feed gas, product gas, or process gas). When the gas used to pressurize the adsorbent bed includes feed gas and/or process gas, a portion of the adsorbed species may be adsorbed in this step. The adsorption step often involves feeding the biogas into the adsorbent bed at a constant pressure and flow rate, thereby preferentially adsorbing the adsorbed species, while a gas stream stripped of the adsorbed species and thus enriched in the unadsorbed species is withdrawn from the opposite end of the adsorbent bed. Blowdown steps often involve rapidly depressurizing the adsorbent bed to a lower pressure counter-currently. In blowdown, part of the adsorbed species may be desorbed, and thus removed from the adsorbent bed. Gas remaining in the adsorbent bed is often rich in the adsorbed species. Purge steps typically involve feeding a purge gas (e.g., product gas at around the lower pressure) through the adsorbent bed counter-currently to desorb and/or remove even more of the adsorbed species (by reducing the partial pressure of the adsorbed species in the adsorbent bed), thereby regenerating the adsorbent bed.

Without being limiting, some advancements that may have improved the purity and/or recovery of the product gases may relate to the use of three or more adsorbent beds, multi-layered adsorbent beds, pretreatments, tanks for storing intermediate process streams between cycle steps (e.g., to use as purge and/or repressurization gas), and/or novel PSA cycle designs. Novel PSA cycle designs may, for example, include up to 10 step cycles, or may introduce additional steps such as pressurization equalization steps. Pressure equalization steps typically include transferring gas in a first adsorbent bed (i.e., that is at the end of the adsorption step and is at the upper pressure) to a second adsorbent bed (i.e., that needs to be pressurized and is at a relatively low pressure). The pressure differential that exists between the first and second adsorbent beds brings the pressure of both the first and second adsorbent beds to an intermediate pressure. Accordingly, pressure equalization steps can increase product recovery and/or reduce compression costs. Unfortunately, pressure equalization steps decrease the productivity of a PSA process. Alternatively, or additionally, novel PSA designs may include various modifications such as selecting between co-current and co-current steps (e.g., using co-current depressurization, where the gas removed during depressurization is used for a pressure equalization step) and/or using one or more evacuation steps (e.g., using a vacuum pump or blower to regenerate the adsorbent bed).

The continuing advances in PSA have contributed to making it more frequently used in biogas upgrading, and more specifically for removing $CO_2$ from biogas. At least some of this success may be attributed to the availability of adsorbents that have good selectivity for $CO_2$ over $CH_4$ or $CH_4$ over $CO_2$ (e.g., carbon molecular sieves (CMS), activated carbon, zeolite, or other materials known in the art). Relative to PSA processes for separating $CO_2$ and $CH_4$, PSA processes for separating $CH_4$ and $N_2$ can be more challenging. For example, $CH_4$ and $N_2$ have relatively similar sizes and/or polarizabilities, and it can be relatively challenging to find adsorbents that provide sufficient selectivity. In U.S. Pat. No. 5,989,316, there is disclosed a Barium-exchanged ETS-4 that shows particular utility in gas separation processes involving the separation of $N_2$ from a mixture of the same with $CH_4$. However, this patent also discloses that the pressure during the adsorption is from about 20 psia to 2000 psia, preferably about 100 to 1500 psia, and more preferably about 500 to 1000 psia. Such elevated pressures can add significant compression costs to the PSA process, and thus may limit its use for biogas upgrading, where processing costs can be a limiting factor. These compression costs may be particularly limiting because the feed gas for biogas upgrading is typically at low pressure (e.g., raw biogas is typically collected at pressures less than 10 psig, and often between 2-3 psig). In addition, costs can also be increased as a result of the installation of multiple parallel adsorbent beds, which may be also required to increase methane recovery and/or methane purity of from the PSA process and/or achieve continuous operation.

In U.S. Pat. No. 10,760,024, Foody et al. disclose a method for providing RNG that includes removing $H_2S$ and/or $CO_2$ from biogas to provide a partially purified biogas that is transported to a biogas upgrading facility in a vessel to be further purified. The pressure of the partially purified biogas in the vessel may be above 1500 psig (e.g., between 2000 psig and 4500 psig). It has now been contemplated that the compressed state of this transported gas (or generally any other gas mixture at high pressure) can be used to reduce the economic challenges and/or tradeoff between product recovery and/or product purity associated PSA, and in particular, with PSA processes for separating at least $N_2$ and $CH_4$.

Figure 2:
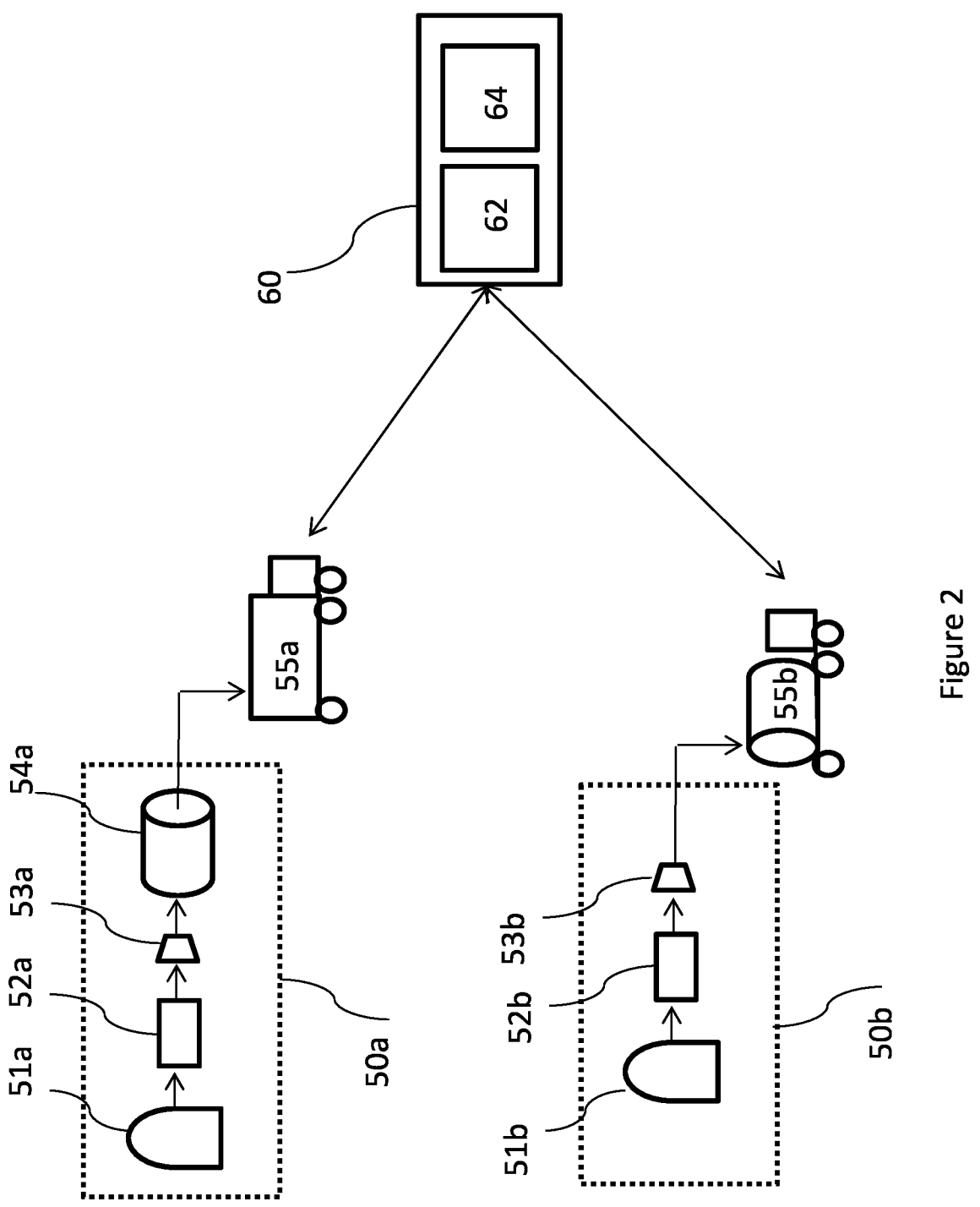
FIG. 2 is a schematic diagram showing a process where biogas is partially purified, compressed, and transported to a processing facility.

FIG. 2 shows a process where biogas produced from multiple geographically spaced landfills 51*a*/51*b* is partially purified at a plurality of pre-processing sites 50*a*/50*b*. The partial purification 52*a*/52*b* removes $H_2S$, $H_2O$, and $CO_2$ and optionally removes VOCs and siloxanes. The partially purified gas is compressed 53*a*/53*b* and fed into one or more vessels (e.g., 54*a*), directly or indirectly via buffer storage. Each of these pressurized vessel(s) may be integrated with or may be coupled with a vehicle (e.g., a tank trailer). Each pressurized vessel is transported by vehicle 55*a*/55*b* to a processing facility 60 (e.g., a centralized processing facility). The processing facility 60 is configured to provide feed preparation 62 and PSA 64 for separating at least $N_2$ and $CH_4$. In this process, the PSA 64 uses an adsorbent selective for $N_2$ over $CH_4$ at elevated pressures (e.g., the PSA process is conducted with an upper pressure of at least 500 psig, such as at least 1000 psig). Preferably, the partial purification 52*a*/52*b* removes $H_2S$, $H_2O$, $O_2$ and/or $CO_2$ to the extent that they do not significantly impact the PSA process and/or negatively affect the quality of the product gas. For example, if the adsorbent does not have good selectivity for $CO_2$ and/or $O_2$ over $CH_4$, then it may be advantageous for the PSA feed to have limited amounts of $CO_2$ and/or $O_2$ (i.e., amounts that still allow the product gas to qualify as RNG). Alternatively, if the adsorbent is capable of removing both $N_2$ and $CO_2$ and/or $O_2$, or if additional $CO_2$ and/or $O_2$ removal is conducted before and/or after the PSA process for separating $N_2$ and $CH_4$ then then the amount of $CO_2$ and/or $O_2$ may not need to be limited during partial purification 52*a*/52*b*. In one embodiment, less than 1%, 2%, 3%, 4%, 5%, or 6% of the biogas feed for PSA is a non-methane component other than $N_2$ (e.g., $CO_2$ and/or $O_2$). Biogas originating from a landfill and subjected to a partial purification to remove most of the $H_2S$, $CO_2$ and/or $O_2$ often has a $CH_4$ content between 60% and 92%, and a $N_2$ content between 40% and 8%. For example, such biogas often has a $CH_4$ content of about 79% and a $N_2$ content of about 21%.

The partially purified biogas transported to the processing facility 60 is at a relatively high pressure (e.g., greater than 500 psig, greater than 1000 psig, greater than 1500 psig, or greater than 2000 psig and up to 4500 psig). Unfortunately, removing (decanting) the biogas from the pressurized vessel(s) may include depressurizing the biogas (e.g., from 4500 psig to 200 psig) such that at least a portion of the biogas is provided at a relatively low pressure and/or such that at least a portion of the biogas is provided with a varying flow rate and/or pressure (e.g., a continuously decreasing pressure or a stepped down pressure (e.g., sawtooth pattern)). Since PSA processes typically include a pressurization step, wherein pressure is increased, and often include adsorption steps that involve providing the feed at a relatively high pressure and constant flow rate, a relatively low pressure and/or varying pressure, and in particular, a decreasing feed pressure, may be unfavourable in terms of providing PSA feed (e.g., may require repressurization). It has now been also contemplated that feed preparation for PSA and/or the PSA cycle itself can be designed to overcome and/or reduce such disadvantages of decanting a gas mixture such as biogas from a pressurized vessel for use as feed for PSA.

The instant disclosure provides method(s) and/or system(s) relating to preparing the feed (i.e., a gas mixture) for PSA processes, where the feed gas is provided in one or more pressurized vessels that need to be decanted (e.g., after transport). These method(s) and/or system(s) are designed to exploit the compressed state of the gas mixture for the PSA process, and thus can reduce the economic challenges and/or tradeoff between product recovery and/or product purity associated with PSA, while reducing compression costs. While these method(s) and/or system(s) can be particularly useful for $N_2/CH_4$ separations, which are often conducted at relatively high pressures, they are also expected to be useful for $CO_2/CH_4$ separations. Furthermore, while these method(s) and/or system(s) can be particularly useful for $N_2/CH_4$ separations where the adsorbent material is selective for $N_2$, they are also expected to be useful for $N_2/CH_4$ separations where the adsorbent is selective for $CH_4$.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The terms "first", "second", etc., may be used to distinguish one element from another, and these elements should not be limited by these terms. The term "plurality", as used herein, refers to two or more. The term "providing" as used herein with respect to an element, refers to directly or indirectly obtaining the element and/or making the element available for use. Unless defined otherwise, all technical and scientific terms used herein have the same meanings as commonly understood by one of ordinary skill in the art.

In the context of describing the combining of components by the "addition" or "adding" of one component to another, or the separating of components by the "removal" or "removing" of one component from another, those skilled in the art will understand that the order of addition/removal is not critical (unless stated otherwise). The terms "remove", "removing", and "removal", with reference to one or more impurities, contaminants, and/or components of biogas, includes partial removal.

The term "biogas", as used herein, refers to a gas mixture that contains $CH_4$ produced from biomass. While biogas is predominately produced by the anaerobic digestion (AD) of organic material, it is also possible to produce biogas from the gasification of biomass. For example, the gasification of biomass may produce syngas, which may be cleaned up, methanated, and separated into methane and carbon dioxide. The term "biogas", as used herein, may refer to raw biogas, partially purified biogas, or renewable natural gas (RNG), unless otherwise specified.

The term "raw biogas", as used herein, refers to biogas as obtained from its source (e.g., anaerobic digester or landfill) before it is treated to remove any chemical components (e.g., $CO_2$, $H_2O$, $N_2$, $H_2S$, $NH_3$, $O_2$, VOCs, and/or siloxanes). Raw biogas may be subjected to biogas upgrading to produce partially purified biogas or RNG.

The term "biogas upgrading", as used herein, refers to a process where biogas is treated to remove one or more non-methane components (e.g., $CO_2$, $N_2$, $H_2O$, $H_2S$, $O_2$, $NH_3$, VOCs, and/or particulates), wherein the treatment increases the calorific value of the biogas. For example, biogas upgrading typically includes removing $CO_2$ and/or $N_2$.

The term "partially purified biogas", as used herein, refers to biogas that has been treated to remove one or more non-methane components (e.g., $CO_2$, $H_2S$, $H_2O$), $N_2$, $NH_3$, $O_2$, VOCs, and/or siloxanes), but requires further treatment in order to meet pipeline specifications (e.g., it may contain one or more non-methane components in an amount that causes it to fall short of meeting natural gas pipeline specifications).

The term "renewable natural gas" or "RNG", as used herein, refers to biogas that has been upgraded to meet or exceed applicable natural gas pipeline specifications, meet or exceed applicable quality specifications for vehicle use (e.g., CNG specifications), and/or natural gas (NG) withdrawn from a NG distribution system that is associated with the environmental attributes of biogas injected into the NG distribution system (e.g., a gas that qualifies as RNG under applicable regulations). Pipeline specifications include specifications required for biogas for injection into a natural gas commercial distribution system. Pipeline quality standards or specifications may vary by region and/or country in terms of value and units. For example, pipelines standards may require the RNG to have a $CH_4$ level that is at least 95% or have a heating value of at least 950 BTU/scf. The percentages used to quantify gas composition and/or a specific gas content, as used herein, are expressed as mol %, unless otherwise specified. More specifically, they are expressed by mole fraction at standard temperature and pressure (STP), which is equivalent to volume fraction.

The term "environmental attributes", as used herein with regard to a specific material (e.g., biogas), refers to any and all attributes related to the material, including all rights, credits, benefits, or payments associated with the renewable nature of the material and/or the reduction in or avoidance of fossil fuel consumption or reduction in lifecycle greenhouse gas emissions associated with the use of the material. Some non-limiting examples of environmental attributes include verified emission reductions, voluntary emission reductions, offsets, allowances, credits, avoided compliance costs, emission rights and authorizations, certificates, voluntary carbon units, under any law or regulation, or any emission reduction registry, trading system, or reporting or reduction program for greenhouse gas emissions that is established, certified, maintained, or recognized by any international, governmental, or nongovernmental agency.

The terms "compressor" or "gas compressor", as used herein, refers to a unit for increasing the pressure of a gas by the application of work, and includes staged compressors and/or multiple compressors arranged in series, in parallel, or combinations thereof.

The term "stream", as used herein with reference to a gas (e.g., gas mixture), is interchangeable with the term "flow", and refers to a moving or still gas in a container (e.g., a pipe, vessel, feed tank, adsorbent bed, and/or processing equipment).

The term "gas mixture", as used herein, refers to a mixture that contains a $CH_4$ component and one or more non-methane components (e.g., $CO_2$ and/or $N_2$) and is in the gas phase at atmospheric temperature and pressures.

The term "raw feed", as used herein with reference to PSA, refers to a gas mixture (e.g., partially purified biogas) that is provided as feed for the PSA process and was not previously withdrawn from an adsorbent bed used in the PSA process (i.e., is not process gas). For example, gas withdrawn from an adsorbent bed and provided for a pressure equalization step is process gas, not feed gas.

The term "pressurized feed", as used herein, refers to raw feed that is at a pressure greater than atmospheric.

The term "pressurizing", as used herein with reference to an adsorbent bed, refers to increasing the pressure in the adsorbent bed (e.g., of the vessel(s) and associated piping).

The term "pressure let down system", as used herein, refers to a system that can reduce the pressure of a gas mixture to a desired level. Pressure let down systems often include one or more mechanical regulating devices (e.g., a pressure regulator or control valve) to reduce the pressure. For example, a pressure let down system may also a pressure regulator, a temperature and/or pressure sensor, one or more valves, a metering system, a control system, and/or temperature control (e.g., heat exchanger). With regard to the latter, the expansion or throttling of a gas provided by a pressure regulator may result in Joule-Thomson cooling of the gas.

The term "adsorbent bed" or "bed", as used herein, refers to a vessel that can be pressurized, contains an adsorbent material, and is configured with an inlet and an outlet. An adsorbent bed may, for example, be a conventional adsorption column having any suitable length to width ratio. In general, the adsorbent material, which may simply be referred to as the adsorbent, is a porous solid, which often has large surface area per unit mass. Each adsorbent bed may contain multiple layers of adsorbent.

The term "properties of the cycle", as used herein with reference to PSA, refers to operating conditions and operating mode of the PSA process. For example, operating conditions can include feed pressure, feed temperature, feed flow rate, feed composition, upper pressure, bed length, bed diameter, bed volume, adsorbent weight, etc. Operating mode can include number of steps, order of steps, step timing, number of beds, etc. The term "upper pressure", as used herein, refers to the highest pressure achieved within an adsorbent bed over the PSA process.

The term "product purity", as used herein, refers to the percentage of the target species in the product gas expressed as a mole percent (e.g., 95% $CH_4$). The term "product recovery", as used herein, refers to the moles of the target species recovered from the process divided by the moles of the target species originally in the feed (e.g., biogas), over a given time period, and is often expressed as a percentage (e.g., 95% $CH_4$ recovery). The term "productivity", as used herein, refers to the quantity of feed processed per volume of adsorbent bed over a given time period (e.g., 55 m³ biogas feed at STP/m³ bed/hr).

In the instant disclosure, a gas mixture (e.g., raw biogas or preferably partially purified biogas) is provided at a pressure that is high relative to the pressures at which biogas is often collected (e.g., 2-3 psig for raw biogas or up to 250 psig for biogas that has been subjected to partial purification). For example, the gas mixture may be pressurized to greater than 300 psig, greater than 400 psig, greater than 500 psig, greater than 600 psig, greater than 700 psig, greater than 800 psig, greater than 900 psig, greater than 1000 psig, greater than 1500 psig, greater than 2000 psig, greater than 1500 psig, greater than 3000 psig, greater than 3500 psig, or greater than 4000 psig. This gas mixture may be pressurized as a result of a biogas collection process where raw biogas is collected, is subjected to a partial purification, is compressed and fed into one or more pressurized vehicles, and is transported in the one or more pressurized vessels by vehicle to a processing site (e.g., a centralized processing site in a hub-and-spoke configuration). In one embodiment, the gas mixture is transported to a processing facility according to a method similar to that described in U.S. Pat. No. 10,760,024 and/or discussed with reference to FIG. 2. The method and/or systems disclosed here are particularly useful for PSA processes that cycle between an upper pressure and a lower pressure, where the upper pressure is greater than 500 psig, and more specifically greater than 1000 psig, and where the lower pressure is relatively close to atmospheric. For example, PSA processes providing $N_2/CH_4$ separations may require high pressures relative to PSA process providing $CO_2/CH_4$ separations. The method and/or systems disclosed here are particularly useful for PSA processes used to upgrade biogas (e.g., raw or partially purified) and more specifically are particularly effective for PSA processes where the feed is partially purified biogas that has been subjected to a $CO_2$ removal and is transported in one or more pressurized vessels by vehicle, and wherein the adsorbent is selective for $CH_4$ over $N_2$ (and optionally over $CO_2$ and/or $O_2$) or selective for $N_2$ (and optionally $CO_2$ and/or $O_2$) over $CH_4$. While methods and/or systems disclosed here are particularly useful for PSA processes used to upgrade biogas, which is conventionally is collected at relatively low pressures, they can also be useful for natural gas upgrading processes where natural gas that needs to be purified is transported in one or more pressurized vessels to a processing facility.

In the instant disclosure, a pressurized gas mixture is depressurized and used to produce a plurality of pressurized feeds, where each pressurized feed has a different average pressure relative to the other pressurized feeds. The pressurized feeds having successively lower average pressures are used to pressurize one or more adsorbent beds in a pressurization step that includes feeding the pressurized feeds into an adsorbent bed in order of increasing average pressure (e.g., in reverse order from which they were produced). The one or more adsorbent bed(s) may be vertical or horizontal and may be operated in series or parallel mode.

Figure 3A:
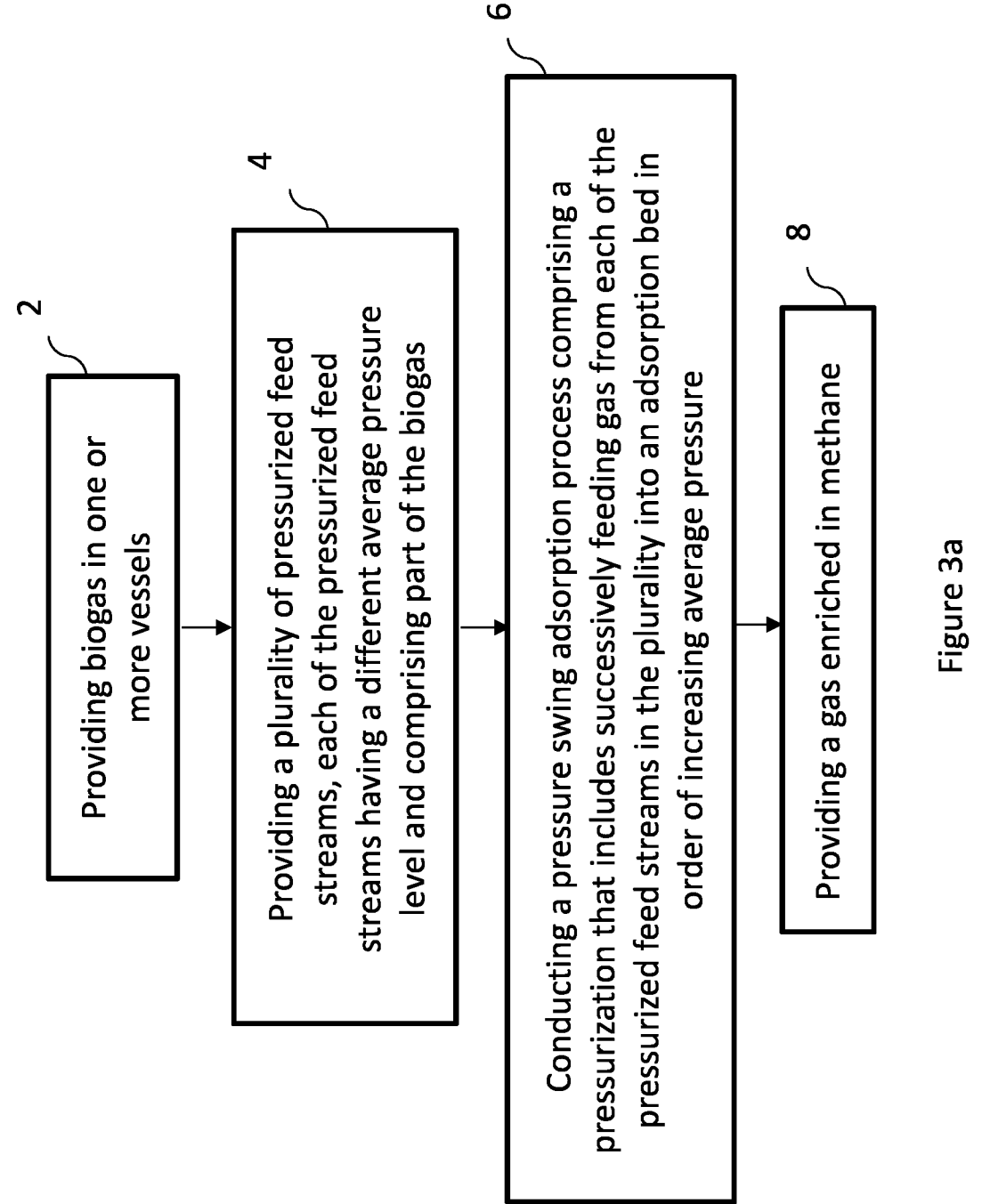
FIG. 3*a* is a flow diagram of a method in accordance with an embodiment of the instant invention.

Various embodiments are described below (e.g., see FIGS. 3a, 3b). Referring to FIG. 3a, there is shown a method according to one embodiment where biogas (e.g., raw or partially purified biogas) is upgraded in a process that includes:

providing biogas in one or more vessels (2);

providing a plurality of pressurized feeds, each of the pressurized feeds having a different average pressure and comprising part of the biogas (4);

conducting a pressure swing adsorption process comprising a pressurization that includes successively feeding gas from each of the pressurized feeds in the plurality into the adsorbent bed in order of increasing average pressure (6); and providing gas enriched in methane from the pressure swing adsorption process (8).

The biogas provided in step 2 includes at least two components (e.g., methane and a non-methane component such as $CO_2$, $N_2$, or $O_2$). In some cases, the biogas has three or more components. For example, some adsorbent beds can be designed to separate $CH_4$ from $CO_2$, $N_2$, and/or $O_2$. The biogas provided in each of the vessels is pressurized.

The plurality of pressurized feeds produced in step 4 is produced in a process that includes decompressing biogas from at least one of the one or more vessels and as the biogas is decompressed providing one or more portions of the biogas at successively lower pressures. In general, any number of pressurized feeds can be produced (e.g., 2 to 20). The biogas can be depressurized within each vessel and/or after being withdrawn from the corresponding vessel. For example, a vessel pressurized at 4000 psig can be depressurized by withdrawing a first portion of the biogas therefrom through a pressure let down system set for 3500 psig, thereby producing a pressurized feed stream at 3500 psig.

In general, each of the pressurized feeds produced in step 4 is provided in and/or from a respective container (e.g., pipe, feed tank, and/or pressurized vessel). Such containers may function as conduits, temporary storage tanks, buffer tanks, and/or surge tanks. Each container in and/or from which one of the pressurized feeds is provided is configured to be in fluid communication with one or more adsorbent beds (e.g., each pipe, feed tank, and/or pressurized vessel may be connected to a manifold that feeds one or more adsorbent beds).

Various approaches for producing the plurality of pressurized feeds are discussed with reference to FIGS. 4a-4f. In the approaches discussed with reference to FIGS. 4a, 4c, and 4f the pressure of each pressurized feed (e.g., in lines 115, 125, 135, 321, 331, 341, 451, 452, 453) decreases with time as the biogas is withdrawn from the respective feed tank (e.g., 110, 120, 130, 320, 330, 340) or pressurized vessel (e.g., 400, 401, 402). Each of these pressurized feeds has an average pressure, which refers to the average of the highest pressure at which the pressurized stream is provided and the lowest pressure at which the pressurized stream is provided. For example, if fluid communication is provided between a feed tank pressurized to 3000 psig and an adsorbent bed pressurized to a lower pressure, then the biogas will flow from the feed tank to the adsorbent bed until the pressure equalizes in both vessels at some intermediate pressure. The average pressure in this case will be the average of 3000 psig and the intermediate pressure. In the approaches discussed with reference to FIGS. 4b, 4d, and 4e, the pressure of each pressurized feed is substantially constant with time as the biogas is withdrawn from the respective feed tank or pressurized vessel. In this case, the average pressure corresponds to the constant pressure.

The PSA process conducted in step 6 uses one or more adsorbent beds, where each bed has at least one adsorbent selective for methane or the non-methane component(s). The adsorbents can be any suitable adsorbent known in the art. For example, adsorbent suitable for separating $CH_4$ from $N_2$ and $CO_2$ may be the Molecular Gate® adsorbent offered by Guild.

The PSA process conducted in step 6 has an adsorption phase wherein the adsorbent bed is pressurized and a desorption phase wherein the adsorbent bed is depressurized. The PSA process includes a pressurization step, typically includes at least one depressurization step and may include other steps (e.g., a feed step, purge step, evacuation step, equalization step, or rest step). As will be understood by those skilled in the art, each of the adsorption phase and desorption phase may include one or more of these steps, or at least part of one or more of these steps. For example, in some Skarstrom-type processes the adsorption phase can correspond to at least part of the pressurization step (e.g., if feed or process gas is used in the pressurization) and a separate feed step (e.g., where feed is fed into the adsorbent bed and a stream enriched in the unadsorbed species is withdrawn). In a novel PSA cycle disclosed herein, the adsorption phase corresponds to at least part of a pressurization step and at least part of a depressurization step.

The PSA process conducted in step 6 includes a pressurization step wherein gas from the pressurized feeds is successively fed into an adsorbent bed in order of increasing average pressure. For example, if there are 4 pressurized feeds, this could include feeding gas from a first pressurized feed having a first average pressure ($P_I$) into the adsorbent bed, followed by feeding gas from a second pressurized feed having a second average pressure ($P_{II}$) into the adsorbent bed, followed by feeding gas from a third pressurized feed having a third average pressure ($P_{III}$) into the adsorbent bed, and followed by feeding gas from a fourth pressurized feed having a fourth average pressure ($P_{IV}$) into the adsorbent bed, where $P_I < P_{II} < P_{III} < P_{IV}$. In the approaches discussed with reference to FIGS. 4a, 4c, and 4f the quantity of gas fed from each feed tank or pressure vessel to the adsorbent bed may correspond to the amount of gas required to achieve the equilibrium pressure. In the approaches discussed with reference to FIGS. 4b, 4d, and 4e, the quantity of gas fed from each pressurized feed may correspond to the amount needed for the adsorbent bed to reach the pressure provided by the pressure let down system.

In step 8 a gas enriched in methane is provided from the pressure swing adsorption process. More specifically, cycling between the adsorption phase and the desorption phase produces a gas stream enriched in methane that can be withdrawn from the adsorbent bed and provided as product gas. Depending on whether the adsorbent(s) used is $CH_4$ selective or selective for the non-methane components, the gas stream enriched in methane may be primarily produced during the adsorption or desorption phase. Using an adsorbent that is selective for the non-methane component(s), such as $N_2$, advantageously can produce at least part of the product gas at a relatively high pressure.

Referring to FIG. 3b, there is shown a method according to one embodiment where biogas (e.g., raw or partially purified biogas) is upgraded in a process that includes:

providing a feed gas comprising biogas, the feed gas pressurized (12);

depressurizing at least a portion of the feed gas, and as the feed gas is depressurized, providing a plurality of pressurized feeds, each of the pressurized feeds in the plurality having a different average pressure (14);

providing the plurality of pressurized feeds to one or more adsorbent beds (16); and subjecting each of the one or more adsorbent beds to a PSA process, the PSA process comprising a pressurization that includes successively feeding gas from the pressurized feeds in the plurality into the adsorbent bed in order of increasing average pressure (18); and providing a gas stream enriched in methane (20).

The feed provided in step 12 is similar to that provided in step 2 (e.g., includes methane and at least one non-methane component such as $CO_2$, $N_2$, or $O_2$). The feed, which may be provided in one or more vessels, is generally pressurized. For example, it may be pressurized to at least 500 psig, at least 600 psig, at least 700 psig, at least 800 psig, at least 900 psig, or at least 1000 psig.

The step of depressurizing at least a portion of the feed gas 14 facilitates providing a plurality pressurized feeds, where each pressurized feed in the plurality has an average pressure that is different than the average pressure of the other pressurized feeds in the plurality. The plurality of pressurized feeds provided in step 14 is similar to the plurality of pressurized feeds provided in step 4. For example, each pressurized feed in the plurality is provided in and/or from a respective container (e.g., pipe, feed tank, and/or vessel). In general, any number of pressurized feeds can be produced (e.g., 2 to 20). Providing a plurality of pressurized feeds, where each pressurized feed in the plurality is provided in and/or from a respective container, allows portions of the feed gas to be withdrawn as the feed is being decompressed and temporarily stored (e.g., in the container) so that they can be provided with increasing average pressures.

In step 16 the plurality of pressurized feeds are provided to one or more adsorbent beds, each of which has at least one adsorbent selective for methane or a non-methane component(s). Each of the one or more adsorbents can be any suitable adsorbent known in the art. For example, adsorbent suitable for separating $CH_4$ from $N_2$ and $CO_2$ may be the Molecular Gate® adsorbent offered by Guild. Each adsorbent bed is configured to be in fluid communication with each line (e.g., pipe) providing one of the pressurized gas streams in the plurality.

In step 18 each of the one or more adsorbent beds is subjected to a PSA process, where each cycle of the PSA process comprises an adsorption phase and a desorption phase, where the adsorption phase includes a pressurization step, the pressurization step including withdrawing at least a portion of gas from one or more of the pressurized feeds, and successively feeding each of the withdrawn portions into the adsorbent bed in order of increasing average pressure.

In step 20, a gas enriched in methane is provided from the PSA process. More specifically, cycling between the adsorption phase and the desorption phase produces a gas stream enriched in methane that can be withdrawn from the adsorbent bed and provided as product gas. Depending on whether the adsorbent(s) used is $CH_4$ selective or selective for the non-methane components, the gas stream enriched in methane may be produced during the adsorption or desorption phase. Using an adsorbent that is selective for the non-methane component(s) advantageously can produce at least part of the product gas at a relatively high pressure.

In the embodiments described with reference to FIGS. 3a and 3b, the PSA process includes successively feeding gas from the pressurized feeds into an adsorbent bed in order of increasing average pressure. In alternate embodiments, each of the pressurized feeds in the plurality may be characterized as having a highest pressure, a lowest pressure, or being capable of providing a given equalization pressure, and the PSA process includes successively feeding the pressurized feeds into an adsorbent bed in order of increasing highest pressure, lowest pressure, or potential equalization pressure. In each embodiment, providing a pressurization step wherein gas from a plurality of pressurized streams is provided in order of increasing average pressure, highest pressure, lowest pressure, or potential equalization pressure, allows the pressure within the adsorbent bed to build to the upper pressure without further compression of the feed, and thus significantly reduces operational costs (e.g., relative to an analogous process where the feed is compressed to bring it up to the upper pressure).

Advantageously, these embodiments facilitate using a higher upper pressure in the PSA process (e.g., higher pressures can be used economically because further compression is not necessarily required). The use of higher pressures can allow the $CH_4$ to be more concentrated, can provide higher productivity, can facilitate the use of equipment with smaller volumes (e.g., smaller adsorbent beds), and/or can reduce complexity of the PSA process. The use of higher pressures in the PSA process can also allow at least a portion of the product gas (e.g., RNG) to be provided at pipeline pressure (e.g., 500 psig-1400 psig), thereby reducing compression costs associated with the product.

Further advantageously, these embodiments and/or the relatively high upper pressure facilitate using simpler PSA cycles and/or equipment. For example, since the transfer of feed gas can be primarily driven by pressure differential (e.g., between the one or more vessels and the one or more feed tanks, between the one or more feed tanks and the one or more adsorbent beds, or between the one or more vessels and the one or more adsorbent beds) the use of compressors and/or pumps for the PSA process can be greatly reduced and/or the operation simplified. Since there is no or reduced compression of the feed gas for the PSA process, cooling systems required to compensate for temperature increases due to high levels of compression can be avoided, further reducing operation costs and/or capital costs. These embodiments also facilitate the use of PSA cycles wherein there is no recompression of an intermediate gas and/or wherein recycle of process gas is avoided.

Various features and/or embodiments of the above described embodiments will be now described in further detail.

Biogas

In general, the biogas in the instant disclosure (e.g., provided in steps 2, 12) is pressurized and provided in one or more vessels. Preferably, the biogas has been pressurized for some reason other than the PSA process (e.g., for transportation purposes). For example, the biogas may originate from one or more biogas sources (e.g., anaerobic digester and/or landfill) and be transported to a centralized processing facility configured for the PSA process as discussed with reference to FIG. 2 (e.g., as raw biogas or partially purified biogas).

The biogas may be pressurized to any suitable pressure. Preferably, the biogas is pressurized to a pressure greater than the upper pressure of the PSA process (e.g., to reduce or avoid recompression of the biogas). Those skilled in the art will understand that the pressure of the biogas may be dependent on the source of biogas, the composition of the biogas, the vessel itself, and/or transportation regulations (e.g., for weight). With regard to the vessel itself, commercially marketed CNG cylinders (e.g., which may be suitable for transporting biogas) often have a nominal pressure rating of 3000 psig at 70° F. (21° C.), 3600 psig at 70° F. (21° C.), or 5000 psig at 70° F. (21° C.). In one embodiment, the biogas is provided in one or more vessels, where each vessel is pressurized to at least 200 psig, at least 300 psig, at least 400 psig, at least 500 psig, at least 600 psig, at least 700 psig, at least 800 psig, at least 900 psig, at least 1000 psig, at least 2000 psig, at least 3000 psig, or at least 4000 psig. Providing biogas pressurized to at least 2000 psig is particularly advantageous for PSA processes providing $N_2/CH_4$ separations (e.g., which may be configured for an upper pressure between 500 psig and 1000 psig, or higher). Providing biogas pressurized to at least 3000 psig, or 4000 psig, is particularly advantageous for facilitating the use of upper pressures greater than 1000 psig and/or facilitating adsorption steps where feed is continuously provided during the adsorption step or when the product gas is obtained during a depressurization step. While the use of upper pressures greater than 1000 psig can improve the product purity and/or product recovery, particularly for $N_2/CH_4$ separations, it can be costly to continuously cycle the adsorbent bed(s) between these high pressures and a lower pressure (e.g., close to atmospheric) using a compressor. However, in the method/system disclosed herein, the pressure can be cycled between these extremes with relatively low or negligible compression costs (e.g., using the feed preparation disclosed herein to exploit the compressed state of the biogas provided for transport).

In general, the biogas can be obtained from any source or combination of sources and can have any composition. For example, the biogas may be raw biogas or partially purified biogas originating from a landfill and/or anaerobic digester. Without being limiting, biogas produced from anaerobic digesters fed agricultural waste may have a $CH_4$ content between about 50% and 75%, whereas biogas from a landfill site may have a CHA content between about 25% and 65%. Biogas produced from a landfill site often has a relatively large $N_2$ content. In one embodiment, the biogas has a methane content between about 25% and 75% and a carbon dioxide content between about 15% and 65%, and the carbon dioxide and methane make up at least 75% of the biogas by volume. In one embodiment, the biogas has a methane content of at least 45%, at least 50%, at least 55%, or at least 60%. In one embodiment, the biogas is predominately $CH_4$ and $N_2$. In one embodiment, the biogas has a $N_2$ content that is at least 5%, at least 10%, at least 15%, or at least 20%, and not greater than 50%, 60%, or 70%. In one embodiment, the biogas is predominately $CH_4$ and $N_2$, and the $CH_4$ and $N_2$ collectively provide at least 96%, at least 97%, at least 98%, or at least 99% of the biogas on a molar basis. In one embodiment, the biogas is predominately $CH_4$, $N_2$, and $CO_2$, where the $CO_2$ content does not exceed 1%, 2%, 3%, 4%, 5%, or 6%. In one embodiment the biogas, which is predominately $CH_4$ and $N_2$, has a $CO_2$ content between about 1% and about 2% and/or a $O_2$ content between about 0% and about 1%.

In embodiments where the biogas is partially purified biogas, it may be produced using any suitable method/technology, or combination of methods/technologies, in one or more stages, as known in the art. For example, $H_2O$ may be removed using a standard biogas dehumidifier, whereas $H_2S$ may be removed using a commercial $H_2S$ removal unit (e.g., based on activated carbon, molecular sieve, iron sponge, water scrubbing, NaOH washing, and/or biofilter or biotrickling filter technologies). Some $H_2S$ may also be removed during the water removal step, if present. $O_2$ may be removed by catalytic oxidation, membranes, or low pressure PSA. $CO_2$ may be removed by absorption (e.g., water scrubbing, organic physical scrubbing, chemical scrubbing), pressure swing adsorption (PSA), membrane permeation, and/or cryogenic upgrading. In one embodiment, the partial purification is essentially a cleaning or pre-cleaning stage that does not significantly remove $CO_2$ or $N_2$. For example, in one embodiment, the partial purification removes $H_2O$ and/or $H_2S$, but does not significantly remove $CO_2$ or $N_2$. In one embodiment, the partial purification removes $H_2O$, $H_2S$, and at least the bulk of the $CO_2$ (e.g., 90% of the $CO_2$). In this embodiment, the remaining $CO_2$ may be removed in a PSA process that separates $CH_4$ from $CO_2$ and $N_2$, and/or may be retained in the product gas. In embodiments where the biogas is partially purified biogas, it can be advantageous for the partial purification to remove sufficient $H_2S$ so that the $H_2S$ does not negatively affect the adsorbent. In one embodiment, the biogas is partially purified biogas that has been subjected to $H_2S$ removal, $H_2O$ removal, VOC removal, and/or siloxane removal. In one embodiment, the biogas is partially purified biogas that has been subjected to $H_2S$ removal, $H_2O$ removal, and $CO_2$ removal.

Feed Preparation

In general, the plurality of pressurized feeds provided in the instant disclosure (e.g., in steps 4 and 14) can be generated using any method and/or feed system that facilitates withdraw of the gas mixture from the one or more vessels and providing the plurality of pressurized feeds (e.g., at the desired average pressures and/or flow rate). For example, the feed system can include high pressure piping, tubing, flexible hose, manifold(s), switching valve(s), coupling(s), compressor(s), ejector(s), mixers, pump(s), check valve(s), control valve(s), pressure regulator(s), temperature and/or pressure sensor(s), metering system(s), control system(s), temperature control(s) (e.g., a heat exchanger), etc. For example, temperature control may be used because the biogas may be a temperature between about-10° C. and 60° C., and it may be beneficial to adjust the temperature (e.g., to ambient temperature(s)).

Various embodiments of methods and/or feed systems and that may be suitable for providing the plurality of pressurized feeds are discussed below and/or are illustrated in FIGS. 4a-4f.

Figure 4A:
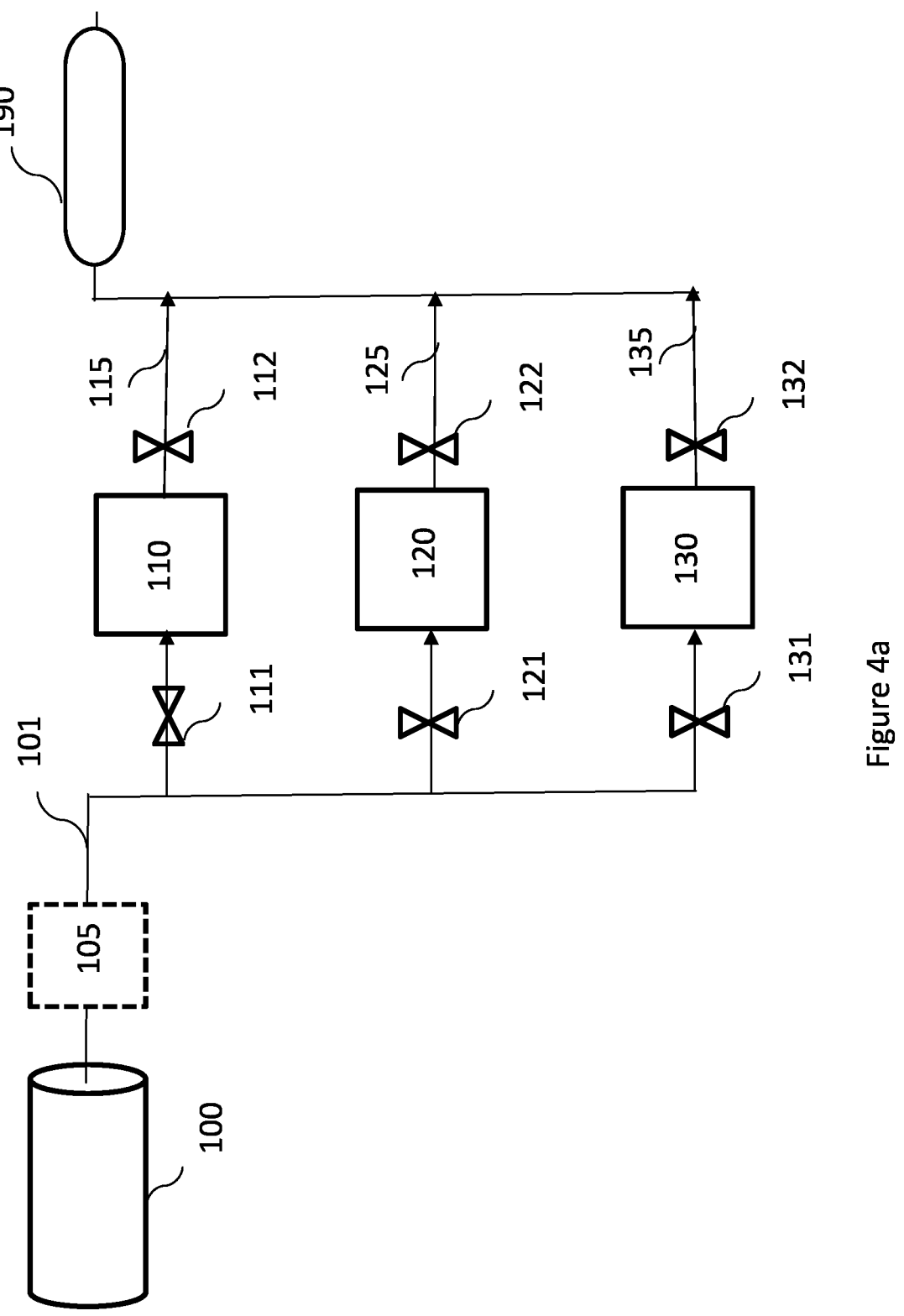
FIG. 4*a* is a schematic diagram showing an embodiment of generating a plurality of pressurized feeds for a PSA process wherein the pressurized feeds are provided from a plurality of feed tanks.

FIG. 4a is a schematic diagram for illustrating a method of producing the plurality of pressurized feeds according to one embodiment. A vessel 100, which contains biogas and is pressurized to a given pressure, is provided. This initial pressure, referred to as $P_i$, can be any suitable pressure (e.g., at least 500 psig, at least 1000 psig, at least 1500 psig, at least 2000 psig, at least 2500 psig, at least 3000 psig, at least 3500 psig, or at least 4000 psig). With valve 111 open and valve 112 closed, a first portion of the biogas flows along line 101 and into a first feed tank 110. The pressure differential between the vessel 100 and the first feed tank 110 drives the biogas into the first feed tank 110 until the pressure equalizes and both the vessel 100 and the first feed tank 110 are at pressure $P_1$. Valve 111 is closed. With valve 121 open and valve 122 closed, a second portion of the biogas flows along line 101 and into a second feed tank 120. The pressure differential between the vessel 100 and the second feed tank 120 drives the biogas into the second feed tank 120 until the pressure equalizes and both the vessel 100 and the second feed tank 120 are at pressure $P_2$. Valve 121 is closed. With valve 131 open and valve 132 closed, a third portion of the biogas flows along line 101 and into a third feed tank 130. The pressure differential between the vessel 100 and the third feed tank 130 drives the biogas into the third feed tank 130 until the pressure equalizes and both the vessel 100 and the third feed tank 130 are at pressure $P_3$. Valve 131 is closed. Accordingly, the feed tanks are filled with biogas at successively lower pressures as the biogas is decanted from the vessel 100 (i.e., $P_1>P_2>P_3$). Optionally, these steps are repeated for the number of vessels available and/or until the vessel 100 is at the lowest pressure (e.g., a heel pressure of 200 psig).

At the appropriate time (e.g., when it is time to pressurize the adsorbent bed 190), the pressurized feeds can be generated. More specifically, valve 132 is opened so that a portion of the biogas in the third feed tank 130 at $P_3$ can flow towards the adsorbent bed 190. The pressure differential between the third feed tank 130 and the adsorbent bed 190 drives the biogas into the adsorbent bed 190 until the pressure equalizes and the third feed tank 130 and the adsorbent bed 190 are at pressure $P_{3e}$ (i.e., $P_3>P_{3e}$) Valve 132 is closed. Valve 122 is opened so that a portion of the biogas in the second feed tank 120 at $P_2$ can flow towards the adsorbent bed 190. The pressure differential between the second feed tank 120 and the adsorbent bed 190 drives the biogas into the adsorbent bed 190 until the pressure equalizes and both the second feed tank 120 and the adsorbent bed 190 are at pressure $P_{2e}$ (i.e., $P_2>P_{2e}$ and $P_{2e}>P_{3e}$). Valve 122 is closed. Valve 112 is opened so that a portion of the biogas in the first feed tank 110 at $P_1$ can flow towards the adsorbent bed 190. The pressure differential between the first feed tank 110 and the adsorbent bed 190 drives the biogas into the adsorbent bed 190 until the pressure equalizes and both the first feed tank 110 and the adsorbent bed 190 are at pressure $P_{1e}$ (i.e., $P_1>P_{1e}$ and $P_{1e}>P_{2e}$). Valve 112 is closed.

In this embodiment, the biogas from the feed tanks is provided to the adsorbent bed 190 as a plurality of pressurized feeds via lines 135, 125, 115 at successively higher average pressures. The pressure of each pressurized feed is referred to as an average pressure because the pressure decreases with time until pressure equalization. The pressurized feed provided from the third feed tank 130 has a pressure close to $P_3$ initially and close to $P_{3e}$ near the end of the equalization. The average pressure of the third pressurized feed is $(P_3+P_{3e})/2$. In each of these embodiments, in addition to reducing or obviating compressions costs associated with the PSA process, incrementally increasing the pressure of the pressurized feeds allows the pressure in the adsorbent bed to gradually build up to the upper pressure (e.g., $P_{1e}$) using pressure equalization type increases but without affecting the productivity of the PSA process (e.g., compared to pressure equalizations between adsorbent beds).

Those skilled in the art will understand that the volumes of the vessels (e.g., 100), feed tanks (e.g., 110, 120, and 130) and adsorbent beds disclosed herein may be selected in dependence, at least in part, upon each other, the number of feed tanks provided, and/or the flow rates. The volumes of the feed tanks may be substantially all the same or may be selected independence upon the quantity of gas needed from different pressures. In one embodiment, the bed volume of each adsorbent bed is similar to the volume of the corresponding feed tank. In one embodiment, the bed volume of each adsorbent bed less than the volume of each of the feed tanks. For example, in one embodiment, the adsorbent beds have bed volumes of about 45 $m^3$, while each feed tank has a volume of about 50 $m^3$. Those skilled in the will also understand the feed tanks are not limited to a particular shape or design and may be any suitable reservoir that can hold the various portions of pressurized feed. For example, each feed tank may be a long and/or large diameter pipe section configured to hold the feed. Those skilled in the art will understand that at least some of the valves described herein (e.g., 112, 122, 132) may be control valves. Using a control valve that provides pressure and/or flow control can be advantageous, particularly at the start of the gas transfer process when the pressure differential is the largest (e.g., in order prevent damage to the adsorbent bed(s)).

Figure 4B:
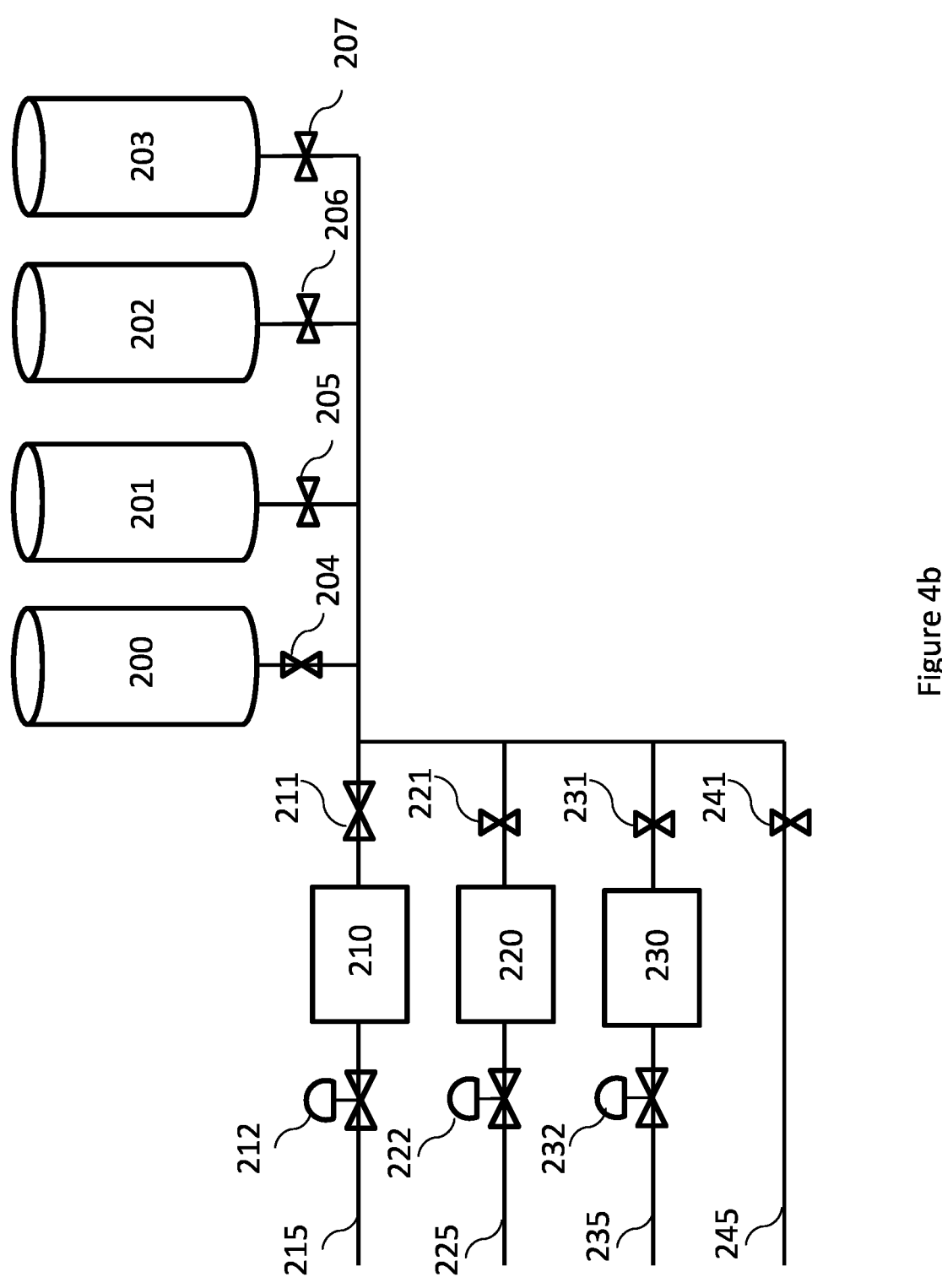
FIG. 4*b* is a schematic diagram showing another embodiment an embodiment of generating a plurality of pressurized feeds for a PSA process wherein the pressurized feeds are provided from a plurality of feed tanks.

FIG. 4b is a schematic diagram for illustrating a method of producing the plurality of pressurized feeds according to another embodiment. In this embodiment, the biogas is provided in a plurality of vessels. For discussion purposes there are 4 vessels, namely 200, 201, 202, and 203. However, more or fewer vessels may be provided. The vessels may contain biogas from a plurality of biogas sources (e.g., each vessel may have been transported from a respective landfill or anaerobic digester) or may be from the same biogas source. If from the same biogas source, the vessels may have been transported using different vehicles or a same vehicle. In the latter case, each vessel may be formed from a plurality of smaller tanks connected by a common manifold.

Each vessel 200, 201, 202, 203 is pressurized to a given pressure. The vessels may be at substantially the same pressure or different pressures. For discussion purposes, each vessel 200, 201, 202, 203 has an initial pressure of $P_i$. The initial pressure $P_i$ can be any suitable pressure (e.g., at least 500 psig, at least 1000 psig, at least 1500 psig, at least 2000 psig, at least 2500 psig, at least 3000 psig, at least 3500 psig, or at least 4000 psig).

With valves 204 and 211 open (and valves 205, 206, 207, 221, 231, and 241 closed) a portion of the biogas from vessel 200 flows along the manifold and into a first feed tank 210. More specifically, the pressure differential between the vessel 200 and the first feed tank 210 drives the biogas into the first feed tank 210 until the pressure equalizes and both the vessel 200 and the first feed tank 210 are at pressure $P_1$. Valve 211 is closed. With valves 204 and 221 open (and valves 205, 206, 207, 211, 231, and 241 closed) another portion of the biogas from vessel 200 flows along the manifold and into the second feed tank 220. More specifically, the pressure differential between the vessel 200 and the second feed tank 220 drives the biogas into the second feed tank 220 until the pressure equalizes and both the vessel 200 and the second feed tank 220 are at pressure $P_2$. With valves 204 and 231 open (and valves 205, 206, 207, 211, 221, and 241 closed) yet another portion of the biogas from vessel 200 flows along the manifold and into the third feed tank 230. More specifically, the pressure differential between the vessel 200 and the third feed tank 230 drives the biogas into the third feed tank 220 until the pressure equalizes and both the vessel 200 and the third feed tank 230 are at pressure $P_3$.

At the appropriate time (e.g., when it is time to pressurize the adsorbent bed (not shown)), the pressurized feeds can be generated. More specifically, biogas is withdrawn from the first feed tank 210 to provide a first pressurized feed via line 215, is withdrawn from the second feed tank 220 to provide a second pressurized feed via line 225, and is withdrawn from the third feed tank 230 to provide a third pressurized feed via line 235. The first pressurized feed in line 215 will be a substantially constant pressure set by pressure let down system 212, the second pressurized feed in line 225 will be a substantially constant pressure set by pressure let down system 222, and the third pressurized feed in line 235 will be a substantially constant pressure set by pressure let down system 232. The average pressures of these pressurized feeds is the substantially constant pressure provided by the corresponding pressure let down system.

In this embodiment, the volume and pressure in each of the feed tanks is selected such that the feed tanks function as buffer tanks and can be replenished by repeating the decanting process for vessels 201, 202, 203. For example, it may be advantageous for each equalization pressure $P_1$, $P_2$, $P_3$ provided by each decanting step to be at least 100 psig, at least 200 psig, or at least 300 psig higher than the corresponding pressure set by the pressure let down system. Advantageously, this embodiment does not require waiting to fill and empty each feed tank before it is used to provide a pressurized feed as each feed can be provided substantially continuously as the corresponding feed tank is replenished. Biogas in the vessels 200, 201, 202, 203 that is present at levels below $P_3$ and/or the corresponding pressure let down system can be fed directly to regenerated adsorbent beds (e.g., at relatively low pressure) using valve 241. For example, such transfer of biogas can be achieved using a pressure equalization to leave each vessel 200, 201, 202, 203 at a pressure corresponding the heel pressure of the vessel (e.g., 200 psig).

Figure 4C:
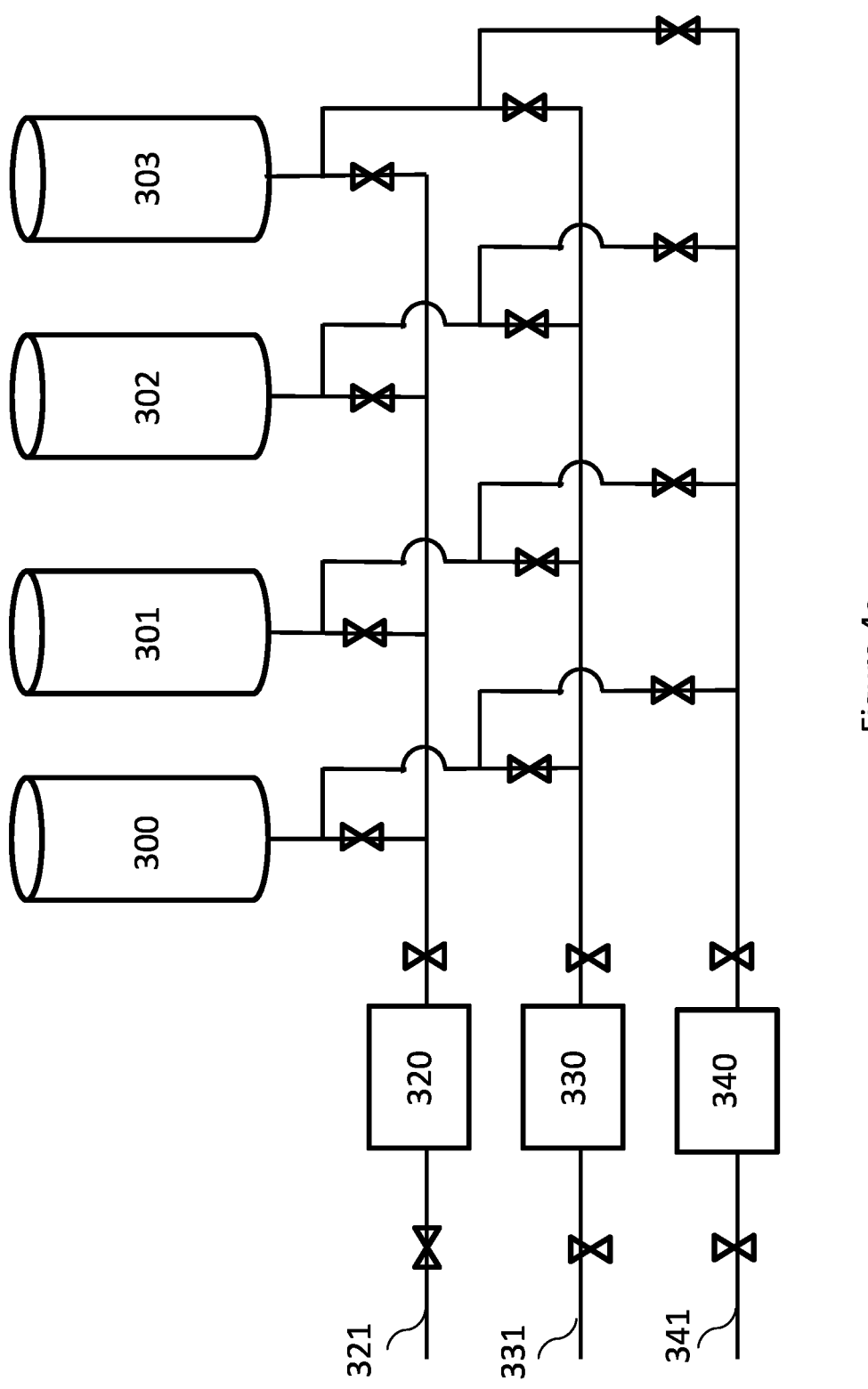
FIG. 4*c* is a schematic diagram showing another embodiment an embodiment of generating a plurality of pressurized feeds for a PSA process wherein the pressurized feeds are provided from a plurality of feed tanks.
Figure 4D:
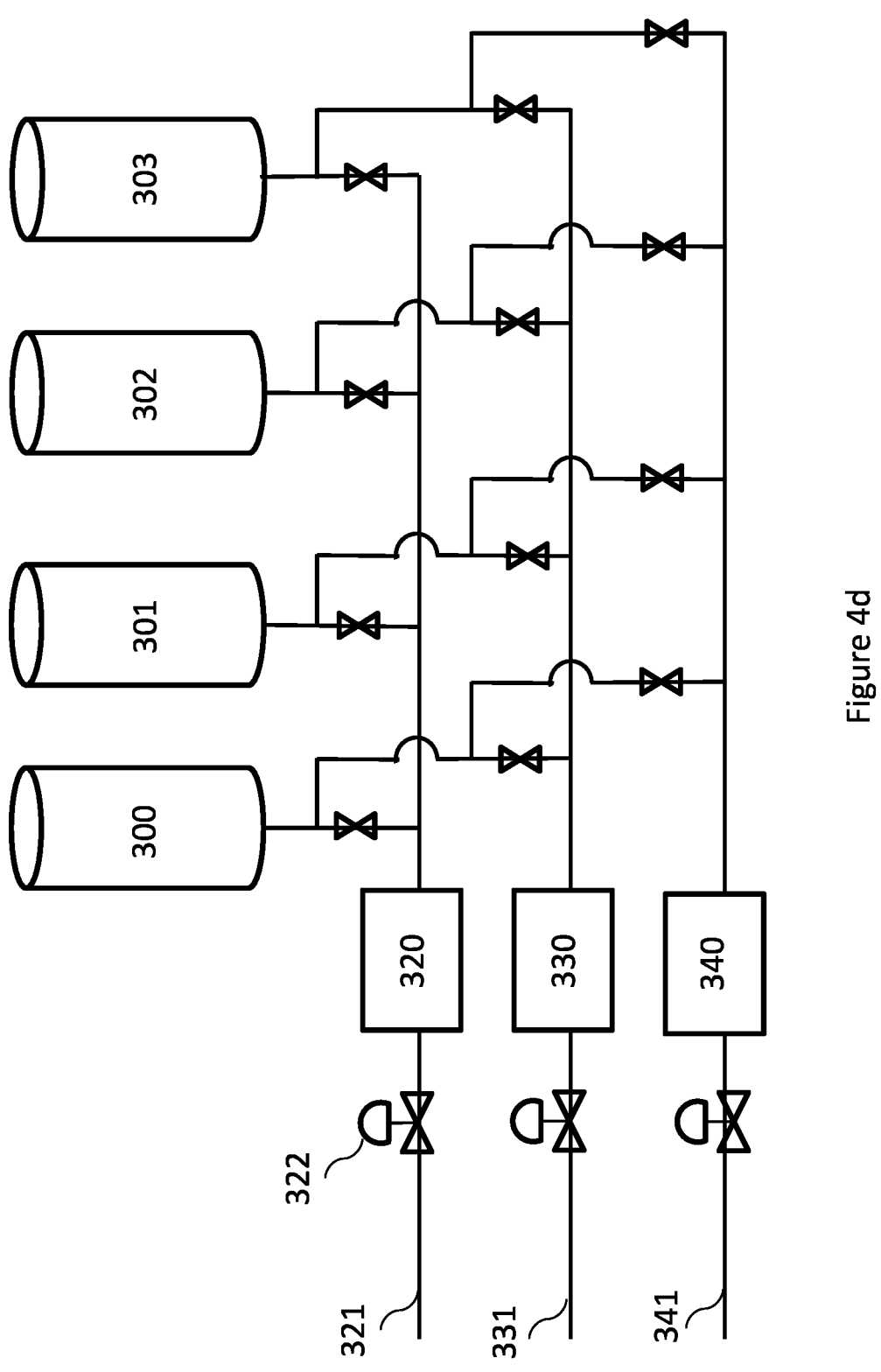
FIG. 4*d* is a schematic diagram showing another embodiment an embodiment of generating a plurality of pressurized feeds for a PSA process wherein the pressurized feeds are provided from a plurality of feed tanks.
Figure 4E:
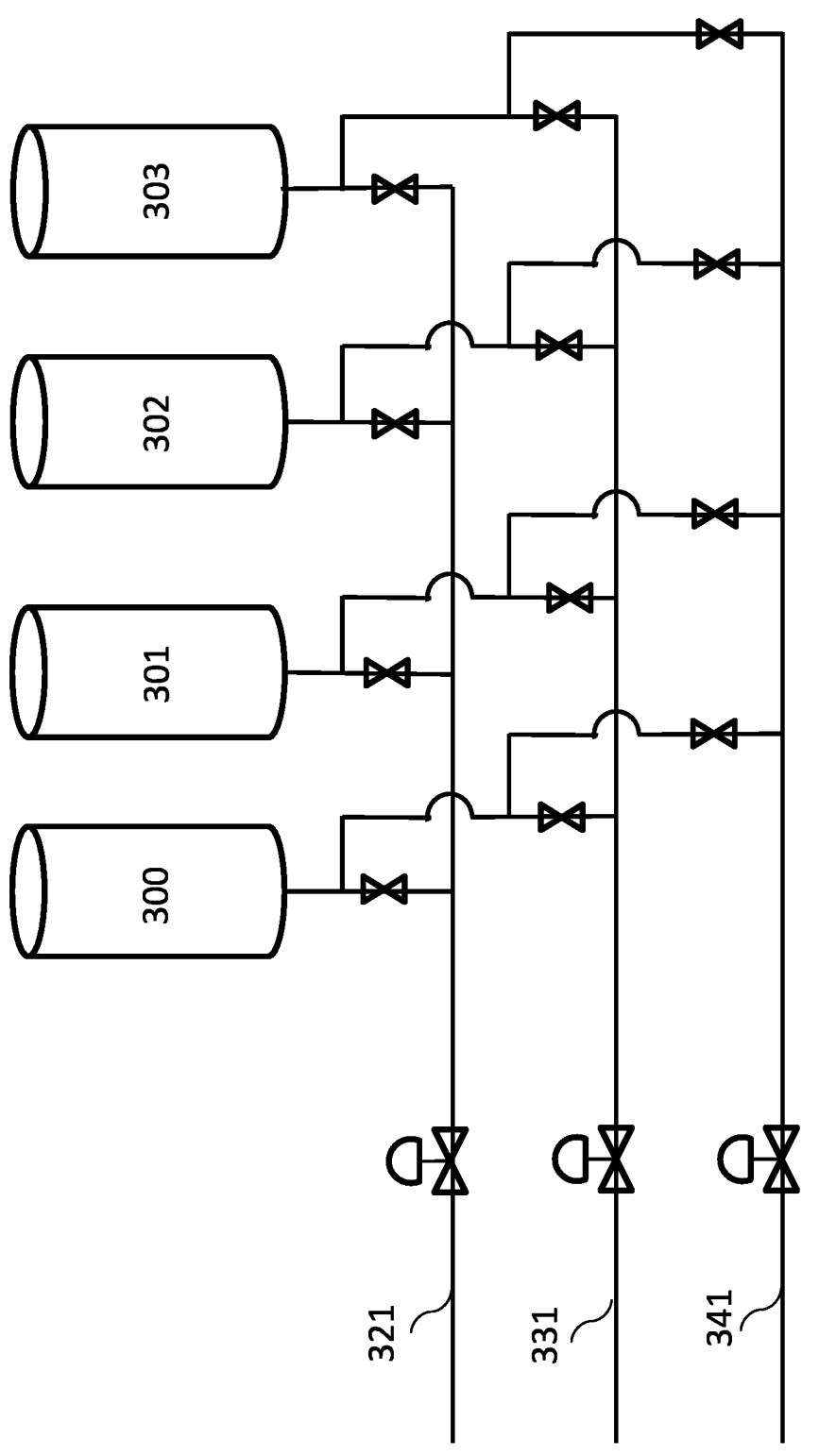
FIG. 4*e* is a schematic diagram showing an embodiment of generating a plurality of pressurized feeds for a PSA process directly from pressurized vessels without using intermediate feed tanks.

FIGS. 4c-4e are schematic diagrams for illustrating various methods of producing the plurality of pressurized feeds according to other embodiments. In each case, the biogas is provided in a plurality of vessels. For illustrative purposes there are 4 vessels, namely 300, 301, 302, and 303. However, more or fewer vessels may be provided. The vessels may contain biogas from a plurality of biogas sources (e.g., each vessel may have been transported from a respective landfill or anaerobic digester) or may be from the same biogas source. If from the same biogas source, the vessels may have been transported using different vehicles or a same vehicle. In the latter case, each vessel may be formed from a plurality of smaller tanks connected by a common manifold.

Each of the vessels 300, 301, 302, and 303 is connected to a configurable manifold. The manifold includes a plurality of valves that can be actuated so that biogas can be simultaneously withdrawn from the vessels 300, 301, 302, and 303 and such that the plurality of pressurized feeds provided via lines 321, 331, 341, each having a different average pressure, can be simultaneously provided. These embodiments are particularly advantageous when the PSA system uses multiple parallel adsorbent beds. Although each vessel will typically start from some initial pressure $P_i$, for the following discussion, the decanting of the vessels 300, 301, 302, and 303 will start when the vessels are at pressures of $P_i$, $P_1$, $P_2$, and $P_i$, respectively (e.g., biogas will have already been decanted from some of the vessels).

Referring to FIG. 4c, the first step includes opening the appropriate valves such that the biogas in the first vessel 300, which is full at $P_i$, begins to flow from vessel 300 into the feed tank 320 where the pressure equalizes at $P_1$. In a second substantially simultaneous step, the appropriate valves are opened such that the biogas in second vessel 301, which has been partially emptied and is at $P_1$, flows from vessel 301 into the feed tank 330 where the pressure equalizes at $P_2$. In a third substantially simultaneous step, the appropriate valves are opened such that biogas in the third vessel 302, which has been partially emptied and is at $P_2$, flows from vessel 302 into the feed tank 340 where the pressure equalizes at $P_3$. Once the valves providing biogas to the feed tanks 320, 330, 340 are closed, the valves to the adsorbent bed(s) can be opened to provide the biogas (e.g., in tandem or simultaneously). Since the feed tanks 320, 330, 340 are ready at substantially the same time, the biogas from each of the feed tanks 320, 330, 340 can fed to a respective adsorbent bed (e.g., wherein each adsorbent bed in at a different step of the process). This process can then be repeated with vessel 300 at $P_i$ and vessel 301 at $P_2$. The third vessel 302, which is substantially empty, is replaced with a substantially full vessel at $P_i$. The fourth vessel 303 at $P_i$ may be used while the third vessel is replaced.

FIG. 4d illustrates an embodiment similar to that in FIG. 4c, except that rather than using the vessels 300, 301, 302 to fill the feed tanks 320, 330, 340 so that they can be used to fill an adsorbent bed by equalization, they are used to maintain each of the feed tanks 320, 330, 340 above a pressure of the corresponding pressure let down system. For example, if feed tank 320 is filled to $P_1$, then the pressure let down system 322 may be set for at least 50 psig lower so that the feed tank may provide sufficient buffering. As will be understood by those skilled in the art, this embodiment can provide all of the pressurized streams substantially simultaneously and substantially continuously (e.g., there may be no discernable interruption in flow of each of the pressurized feeds provided).

FIG. 4e illustrates an embodiment similar to that in FIG. 4d, except that the use of the feed tanks 320, 330, 340 is avoided. In this embodiment, rather than providing the biogas through a pressurization equalization step, the pressurized feed 321 is constantly withdrawn from vessel 300 at $P_i$ as the pressure within the vessel 300 falls from $P_i$ to $P_1$. The valves are then actuated such the pressurized feed 331 is constantly withdrawn from vessel 300 at $P_2$ as the pressure within the vessel 300 falls from $P_i$ to $P_2$. This actuation of the valves also allows the substantially continuous production of pressurized feed 321 as biogas is withdrawn from vessel 301 at $P_i$ as the pressure within the vessel 300 falls from $P_i$ to $P_1$.

Figure 4F:
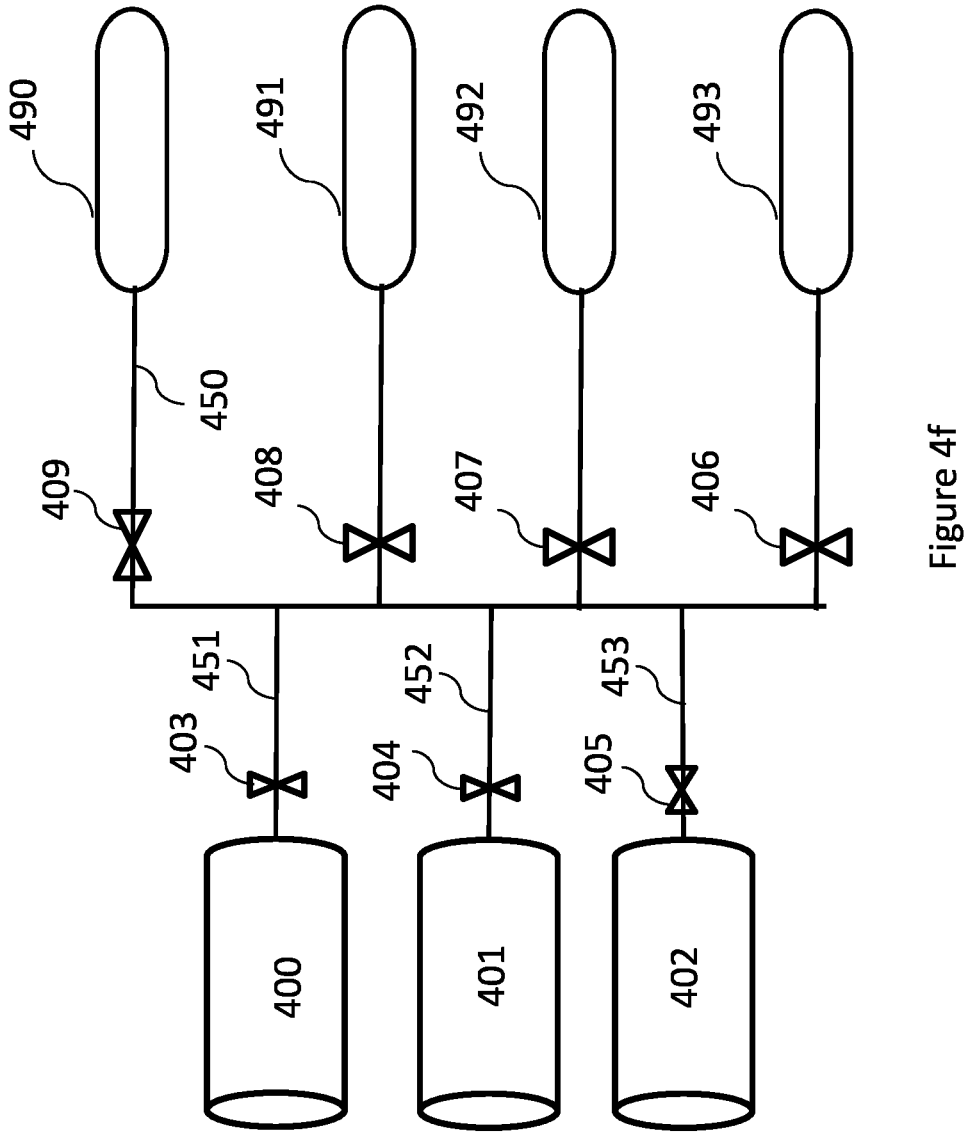
FIG. 4*f* is a schematic diagram showing another embodiment of generating a plurality of pressurized feeds for a PSA process directly from pressurized vessels without using intermediate feed tanks.

FIG. 4f illustrates yet another embodiment, where the use of separate feed tanks is avoided. In this embodiment, the biogas is provided in a plurality of vessels. For illustrative and discussion purposes there are 3 vessels, namely 400, 401, and 402. However, more or fewer vessels may be provided. The vessels may contain biogas from a plurality of biogas sources (e.g., each vessel may have been transported from a respective landfill or anaerobic digester) or may be from the same biogas source. If from the same biogas source, the vessels may have been transported using different vehicles or a same vehicle. In the latter case, each vessel may be formed from a plurality of smaller tanks connected by a common manifold.

Although each vessel will typically start from some initial pressure $P_i$, for discussion purposes the decanting of the vessels 400, 401, and 402 will start when the vessels are at pressures of $P_i$, $P_i$, and $P_2$, respectively. In this embodiment, vessel 400 may correspond to a full vessel at $P_i$ recently delivered for processing. For example, the initial pressure $P_i$ can be any suitable pressure (e.g., at least 500 psig, at least 1000 psig, at least 1500 psig, at least 2000 psig, at least 2500 psig, at least 3000 psig, at least 3500 psig, or at least 4000 psig). Vessels 401 and 402 may correspond to vessels from which some biogas has already been decanted.

With valves 405 and 409 open (and valves 403, 404, 406, 407, 408 closed) the biogas in vessel 402 flows along line 453 and into a first adsorbent bed 490. As the biogas in the vessel 402 is initially at $P_2$ and the adsorbent bed is initially at about atmospheric pressure (e.g., between 0 and 2 atm absolute pressure), the pressure differential between the vessel 402 and the adsorbent bed 490 drives the biogas into the adsorbent bed until the pressure equalizes and both the vessel 402 and the adsorbent bed 490 are at $P_{2e}$. For example, $P_{2e}$ may be at about 200 psig (e.g., the heel pressure of the vessel). Valve 405 is closed. With valves 404 and 409 open (and valves 403, 405, 406, 407, 408 closed) the biogas in vessel 401 flows along line 452 and into the first adsorbent bed 490. As the biogas in vessel 401 is initially at $P_1$, and $P_1$ is greater than $P_{2e}$, the pressure differential between the vessel 401 and the adsorbent bed 490 drives the biogas into the adsorbent bed until the pressure equalizes and both the vessel 401 and the adsorbent bed 490 are at Pie. Valve 404 is closed. With valves 403 and 409 open (and valves 404, 405, 406, 407, 408 closed) the biogas in vessel 400 flows along line 451 and into the first adsorbent bed 490. As the biogas in the vessel 400 is initially at $P_i$, and $P_i$ is greater than Pie, the pressure differential between the vessel 400 and the adsorbent bed 490 drives the biogas into the adsorbent bed until the pressure equalizes and both the vessel 400 and the adsorbent bed 490 are at Pie. Valve 403 is closed. In this embodiment, the upper pressure in the PSA process is Pie. As the vessels switch between $P_i$, $P_1$, and $P_2$, additional adsorbent beds can be pressurized in a similar manner.

In general, any number of pressurized feeds may be provided. For example, in this embodiment, the number of pressurized feeds is at least 2 and not more than 20. In one embodiment, the number of pressurized feeds is 2, 3, 4, 5, 6, 7, 8, 9, 10, or higher. Providing at least 5, 6, 7, 8, 9, or 10 pressurized feeds is advantageous in terms of exploiting as much of the compressed state of the biogas as possible. Providing at least 5, 6, 7, 8, 9, or 10 pressurized feeds may also accommodate utilizing more of the biogas at lower pressures (e.g., near the end of the biogas decanting) and/or increasing the possible pressure of the pressurized feeds at the highest pressure. Those skill in the art will understand that the number of pressurized feeds and volume of each pressurized feed may be dependent on the volumes of the vessels, volume of feed tanks, volume of adsorbent beds, the number of feed tanks, and/or the number of adsorbent beds.

In the above described embodiments, the pressurized feeds may be transferred via different conduits (e.g., lines and/or feed tanks). Pressurizing an adsorbent bed using pressurized feeds transferred at least partially using different conduits is a unique approach to addressing using feed having a generally decreasing pressure to increase the pressure in an adsorbent bed.

Advantageously, the above described embodiments are particularly useful when the feed is biogas transported using mobile pressure vessels coupled to a vehicle (e.g., truck, rail, ship), and more specifically when the feed is collected as part of a collection process that provides biogas from multiple sources to a centralized processing facility. In general, such biogas may have been processed (e.g., subjected to partial purification) prior to transport, and thus may have a composition suitable for a PSA process that provides an $N_2/CH_4$ separation. In addition, providing one or more feed tanks that function as buffer and/or surge tanks, can compensate for any inconsistencies in delivery time, initial vessel pressure, and/or gas composition caused by sourcing the biogas from multiple sources. While the biogas may be processed 105 prior to the PSA process, it may be advantageous provide any further processing, if required, after the PSA process.

Further advantageously, the above described embodiments result in at least a portion of the biogas being only minimally decompressed (e.g., the pressurized feed having the highest average pressure). Since some of the biogas is only minimally decompressed, a smaller volume of gas will be processed (e.g., relative to if all of the biogas was expanded), which may reduce equipment costs. While these embodiments have been discussed using a biogas feed, the feed can be any gas mixture.

Pressure Swing Adsorption

In general, the pressure swing adsorption (PSA) process(es) of the instant disclosure can use any suitable adsorption material or combination of adsorption materials known in the art that can separate methane from one or more non-methane components of the gas mixture. Adsorption materials used for upgrading gas mixtures containing methane, such as biogas, are well known in the art and may be available commercially. For example, $CO_2$ selective adsorbents may contain and/or be based on activated carbon, zeolites such as 5A, molecular sieve carbons, silica gel, or activated alumina. $N_2$ selective adsorbents may contain titanosilicate (e.g., Molecular Gate® offered by Guild). The Molecular Gate® technology, which has a relatively high design pressure (e.g., about 825 psig), contains titanosilicate ETS-4 tailored as a $N_2$ selective molecular sieve. Advantageously, the Molecular Gate® technology can separate $CH_4$ from both $N_2$ and $CO_2$ (e.g., preferentially adsorbing $CO_2$ over $N_2$). $CH_4$ selective adsorbents containing activated carbon often adsorb $CH_4$ and $CO_2$, while letting both $N_2$ and $O_2$ pass at about the feed pressure.

The PSA process(es) of the instant disclosure (e.g., in steps 6, 18) includes a pressurization step wherein feed gas (i.e., raw feed) is fed into an adsorbent bed to pressurize the adsorbent bed. The pressurization step includes feeding a plurality of pressurized feeds having different average pressures into the adsorbent bed in order of increasing average pressure. While such processes do not exclude the option of also pressurizing the adsorbent bed with process gas (e.g., gas removed from an adsorbent bed during depressurization) and/or product gas, one advantage of the system/methods described herein is that pressurizing the adsorbent bed with only pressurized feed, or primarily pressurized feed, can improve the productivity of the PSA process and/or utilize the portion of the feed at lower pressures without requiring compression. In one embodiment, only feed gas is used for pressurizing the adsorbent bed. In one embodiment, feed gas is primarily used for pressurizing the adsorbent bed. In one embodiment, feed gas makes up at least 40%, at least 50%, at least 60%, at least 70%, at least 80%, or at least 90% of the gas used to pressurize the adsorbent bed, by mass. Providing a configuration where feed gas makes up about 50%, or about 60% of the feed gas, may increase methane recovery.

The pressure swing adsorption (PSA) process in the instant disclosure (e.g., in steps 6, 18) can be based on any PSA process known in the art. The PSA process will typically include cycling an adsorbent bed between at least an adsorption phase and a desorption phase. In the adsorption phase, which may be conducted over one or more steps, the adsorbed species is preferentially adsorbed on the adsorbent bed. For example, the adsorption phase may span a pressurization step, an adsorption step, and/or a depressurization step (e.g., part of the depressurization). In the desorption phase, which may also be conducted over one or more steps, the adsorbed species is desorbed. For example, the desorption phase may span at least a depressurization step, a purge step, and/or an evacuation step. In general, the PSA process(es) can be carried out using a single adsorbent bed or a plurality of adsorbent beds.

Figure 5A:
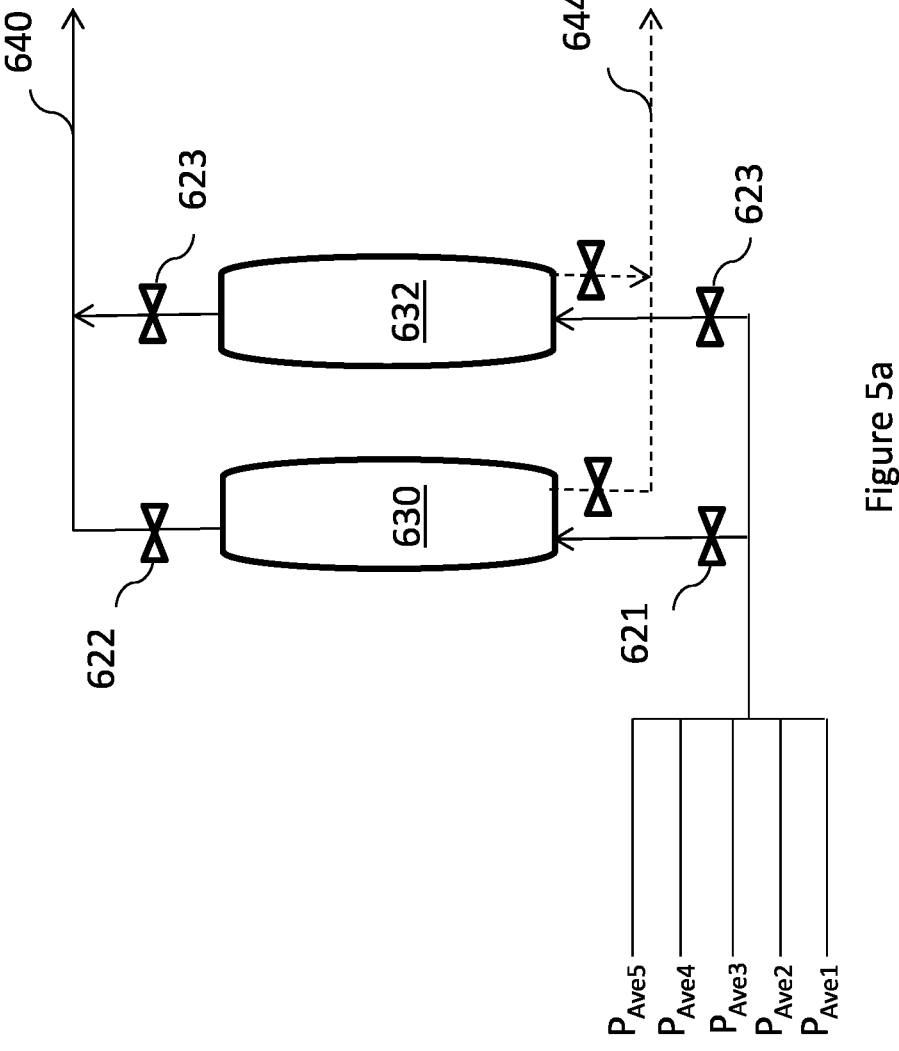
FIG. 5*a* is a schematic diagram showing an embodiment of a PSA system according to one embodiment.
Figure 5B:
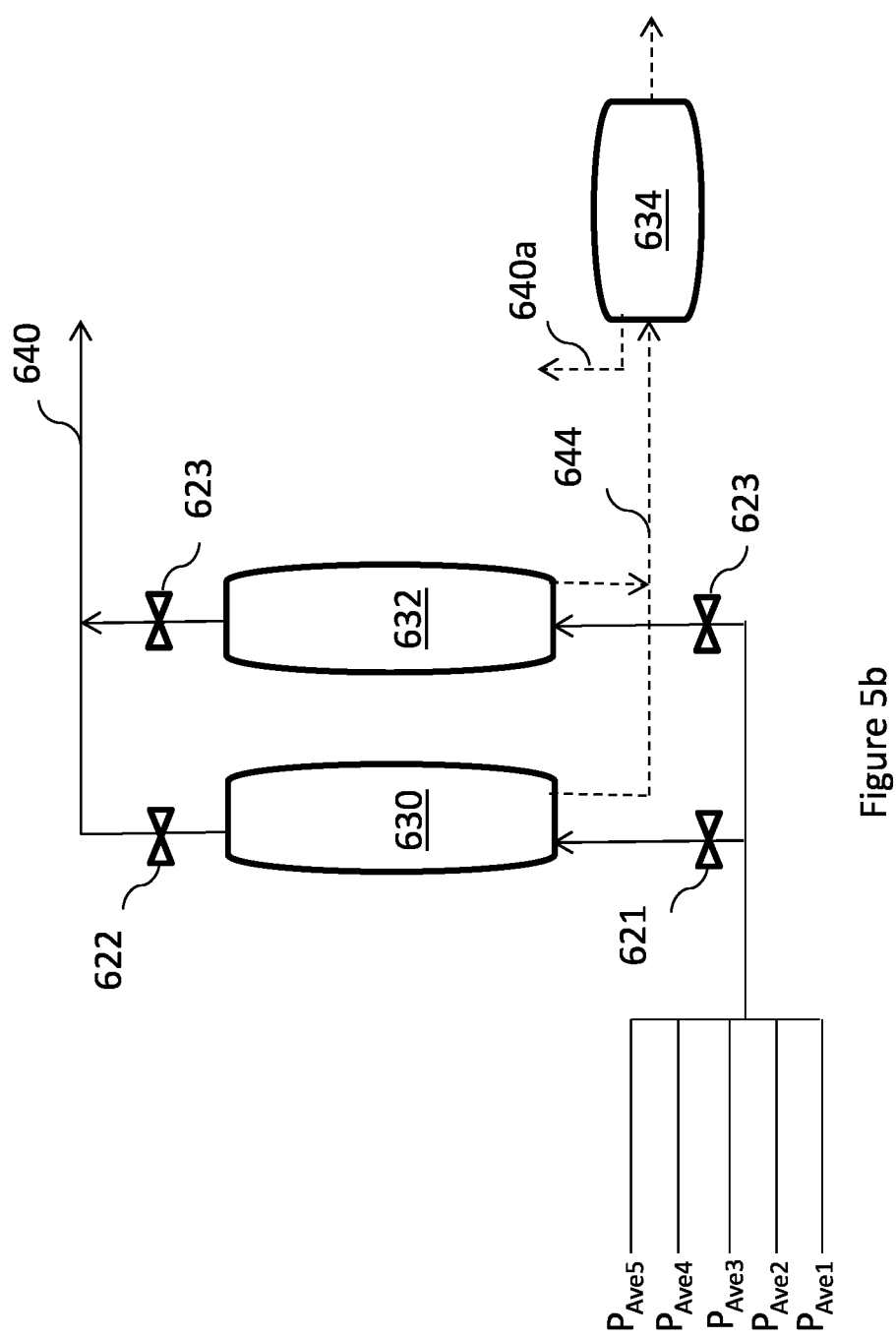
FIG. 5*b* is a schematic diagram showing another embodiment of a PSA system according to one embodiment.

Various embodiments of PSA process(es) that may be suitable for processing the plurality of pressurized feeds will now be discussed with reference to the representative systems illustrated in FIGS. 5a and 5b. In these systems, the adsorbent in beds 630 and 632 is a $N_2$ selective adsorbent (i.e., preferentially adsorbs $N_2$ over $CH_4$) and the feed is partially purified biogas that is predominately $CH_4$ and $N_2$ (e.g., 79% $CH_4$ and 21% $N_2$). The feed is provided as a plurality of pressurized feeds having different average pressures (i.e., $P_{Ave1}$ to $P_{Ave5}$).

A PSA process according to one embodiment includes the following steps.

(a) With the adsorbent bed 630 being in a regenerated state, and with valve 621 open, the pressurized feed having the lowest average pressure $P_{Ave1}$ is fed into the adsorbent bed 630, followed by the pressurized feed having the second lowest average pressure $P_{Ave2}$, the pressurized feed having the third lowest average pressure $P_{Ave3}$, the pressurized feed having the fourth lowest average pressure $P_{Ave4}$, and the pressurized feed having the highest average pressure $P_{Ave5}$. In general, valve 622 is closed to the extent that the successively fed pressurized feeds can build up the pressure within the adsorbent bed (i.e., to the upper pressure) and/or maintain the pressure at the upper pressure). During at least the latter part of this step, valve is open to the extent that a product stream enriched in $CH_4$ can be withdrawn as product gas 640.

(b) Once the adsorbent bed 630 is substantially saturated with $N_2$, or prior to significant breakthrough of $N_2$, valves 621 and 622 are closed. The adsorbent bed is then depressurized by withdrawing the gas therein through line 644. Although the depressurization may result in the adsorbent bed being close to atmospheric pressure near the end of the depressurization step, the adsorbent bed may still contain a significant amount of $CH_4$ and/or $N_2$ (e.g., in the void space). Optionally, a purge step and/or evacuation step is conducted on the adsorbent bed and the gas produced by such step(s) is provided as off-gas in line 644.

While adsorbent bed 630 is undergoing step (b), the other adsorbent bed 632 can be undergoing a step analogous to step (a). Steps (a) and (b) are repeated for each adsorbent bed. In general, the gas extracted in line 644 from the depressurization, purge step, and/or evacuation step can be collected, disposed of, and/or further treated. Since the gas extracted in line 644 can contain a significant amount of $CH_4$, it can be advantageous to further treat it and thus improve product recovery. In the embodiment in FIG. 5b, the gas extracted in line 644 is fed to an adsorbent bed 634 having a $CH_4$ selective adsorbent, thereby providing additional $CH_4$ product 640a. In this case, the $CH_4$ product is provided from the desorption phase. Optionally, the feed for the adsorbent bed having the $CH_4$ selective adsorbent 634 is produced in a process that includes producing a plurality of feed streams having successively lower pressures as the adsorbent bed 630 is subjected to the depressurization step. This embodiment may be particularly suitable for use with the feed preparation embodiments discussed with reference to FIG. 4b, 4d, or 4e as the pressure let down systems may facilitate providing feed at a constant pressure and flow rate for any steps that include feeding the pressurized feeds into one end of adsorbent bed and simultaneously withdrawing product from the other end (e.g., an adsorption step).

A PSA process according to another embodiment includes the following steps.

(a') With the adsorbent bed 630 being in a regenerated state, and with valve 621 open and valve 622 closed, the pressurized feed having the lowest average pressure $P_{Ave1}$ is fed into the adsorbent bed 630, followed by the pressurized feed having the second lowest average pressure $P_{Ave2}$, the pressurized feed having the third lowest average pressure $P_{Ave3}$, the pressurized feed having the fourth lowest average pressure $P_{Ave4}$, and the pressurized feed having the highest average pressure $P_{Ave5}$. Valve 622 remains closed during the entire pressurization step until the upper pressure is reached. While adsorption does occur, no product is made during this step.

(b') Once the adsorbent bed 630 reaches the upper pressure, valve 621 is closed and valve 622 is opened, thereby producing a stream enriched in $CH_4$ that is withdrawn as product gas 640. While adsorption may occur, no feed is fed into the adsorption column during this step. For example, when the feed step is terminated well before saturation of the adsorbent bed, $N_2$ may continue to be adsorbed as the gas mixture passes through the adsorbent bed during the depressurization, thereby increasing product purity. Prior to significant breakthrough of $N_2$, valve 622 is closed.

(c') The adsorbent bed is then further depressurized by withdrawing the gas therein through line 644. Although this second depressurization step may result in the adsorbent bed being close to atmospheric pressure near the end thereof, the adsorbent bed may still contain a significant amount of $CH_4$ and/or $N_2$ (e.g., in the void space). Optionally, a purge step and/or evacuation step is conducted on the adsorbent bed and the gas produced by these steps is provided as off-gas in line 644. Alternatively, the novel approach discussed in Example 1 is used to improve the product recovery and/or purity.

While adsorbent bed 630 is undergoing step (c'), the other adsorbent bed 632 can be undergoing a step analogous to step (a'). Steps (a'), (b'), and (c') can be repeated for each adsorbent bed. Optionally, at least three adsorbent beds are provided, wherein each adsorbent bed can be used for one of the process steps. In general, the gas extracted in line 644 from the depressurization, purge step, and/or evacuation step can be disposed of or further treated. Since the gas can contain a significant amount of $CH_4$, it can be advantageous to further treat it and thus improve product recovery. For example, the gas extracted line 644 can be fed to an adsorbent bed 634 having a $CH_4$ selective adsorbent, thereby providing additional $CH_4$ product 640a, as illustrated in FIG. 5b. In this case, the $CH_4$ product is provided from the desorption phase. Optionally, the feed for the adsorbent bed having the $CH_4$ selective adsorbent 634 is produced in a process that includes producing a plurality of feed streams having successively lower pressures as the adsorbent bed 630 is subjected to the depressurization step.

This PSA cycle includes at least three phases, namely, (1) a pressurization phase where the adsorbent bed is pressured to an upper pressure and where no product gas is withdrawn (2) once the upper pressure is reached, a first depressurization phase in which product gas is withdrawn, and (3) a second depressurization phase that reduces the pressure to close to atmospheric. Optionally, the cycle includes a regeneration phase (e.g., including one or more purge steps and/or evacuation steps) following the second depressurization phase.

Advantageously, the combination of the first two phases can provide product gas that requires little to no compression prior to injection into a natural gas distribution system, while the third phase can be designed to increase overall methane recovery and/or overall methane purity (e.g., including purity of product gas produced from the gas withdrawn during the second depressurization). For example, at least part of the gas withdrawn during the third phase can be (i) used within the process, (ii) further treated (e.g., to provide additional product gas and/or be used within the process), and/or (iii) disposed of.

Figure 6:
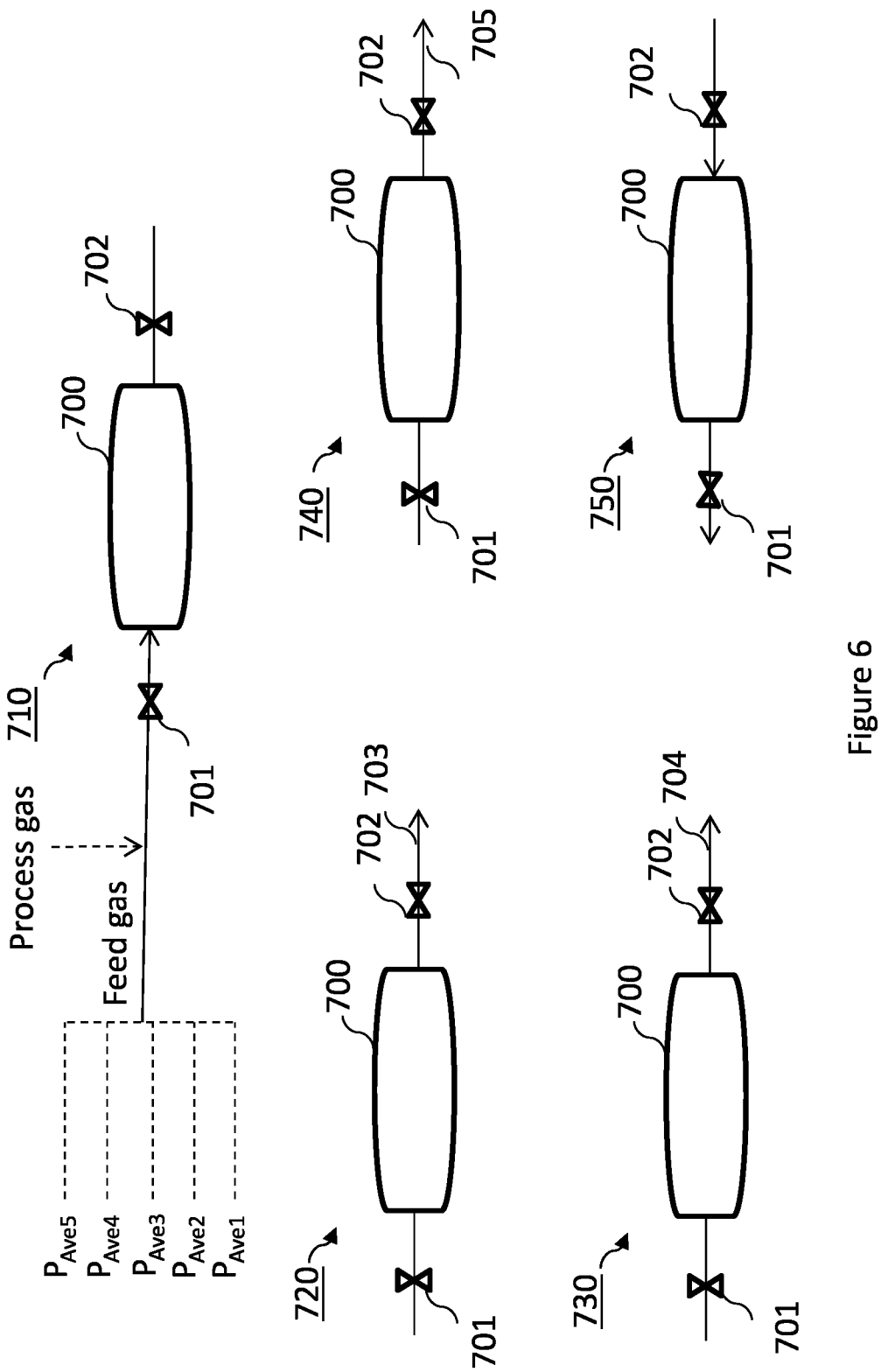
FIG. 6 is a schematic diagram showing an embodiment of a PSA process.

Referring to FIG. 6, there is shown a PSA process according to another embodiment, including a PSA cycle having at least four phases. The adsorbent in bed 700 is a $N_2$ selective adsorbent (i.e., preferentially adsorbs $N_2$ over $CH_4$) and the feed is partially purified biogas that is predominately $CH_4$ and $N_2$ (e.g., 80% $CH_4$ and 20% $N_2$). Optionally, the feed gas is provided as a plurality of pressurized feeds having different average pressures (i.e., $P_{Ave1}$ to $P_{Ave5}$).

In the first phase 710, which is a pressurization phase, the adsorbent bed 700 is pressurized to a relatively high pressure (e.g., greater than about 500 psig, greater than about 600 psig, greater than about 700 psig, greater than about 800 psig, greater than about 900 psig, greater than about 1000 psig and/or up to about 3600 psig). In general, this is achieved by passing gas through valve 701 while valve 702 is closed. The bed 700 may be pressurized to this upper pressure using only feed gas or using a combination of feed gas and process gas (e.g., gas withdrawn from an adsorbent bed in another phase of this cycle and/or from another adsorbent bed having a different cycle). The pressurization may be continuous and/or stepped (e.g., based on the pressure equalization discussed above). For example, in certain embodiments, the feed gas is provided as a plurality of pressurized feeds ($P_{Ave1}$-$P_{Ave5}$) and the pressurization is achieved by feeding a pressurized feed having the lowest average pressure $P_{Ave1}$ into the adsorbent bed 700, followed by the pressurized feed having the second lowest average pressure $P_{Ave2}$, the pressurized feed having the third lowest average pressure $P_{Ave3}$, the pressurized feed having the fourth lowest average pressure $P_{Ave4}$, and the pressurized feed having the highest average pressure $P_{Ave5}$. In certain embodiments, the feed gas is provided as a continuous pressurized feed. For example, in such embodiments, the feed gas may be withdrawn from a pressurized vessel pressurized (e.g., at about 800 psig or higher), through a pressure let down system set to the upper pressure (e.g., 500 psig).

No product gas is withdrawn from the adsorbent bed 700 during this pressurization phase (i.e., no gas is withdrawn from the adsorbent bed as it is being pressurized). In general, this first phase can continue for any suitable time. For example, it can continue until the pressure reaches the upper pressure (i.e., the highest pressure achieved during the cycle) or for some time after that. For example, in certain embodiments, the first phase may include an equilibration period after the upper pressure is reached (i.e., where both the first 701 and second 702 valves are closed). The adsorbent bed contains adsorbent and void space. At the end of the first phase, the concentration of nitrogen in the void space may follow a gradient such that the nitrogen content is highest near the left-hand side (i.e., feed end) and lowest near right-hand side (i.e., product end) of the adsorbent bed (e.g., concentration of more strongly adsorbed component is typically higher near the inlet). Similarly, the concentration of methane in the void space may follow a gradient where the methane content is highest near the product end and lowest near the feed end of the adsorbent bed (i.e., concentration of less strongly adsorbed component is typically higher near the outlet).

In the second phase 720, which is a depressurization phase, the adsorbent bed 700 is depressurized in one or more steps to provide product gas 703. Each depressurization step involves withdrawing gas from the adsorbent bed 700 through the first valve 701 and/or the second valve 702. It can be particularly advantageous to withdrawal gas through the second valve 702 in this phase (e.g., a co-current depressurization with respect to the feed direction as shown in FIG. 6) as it may improve purity of the product gas 703. For example, since the concentration of nitrogen in the void space can vary as a function of distance from the inlet, this allows the gas having the highest methane content to be withdrawn first. In addition, as the gas near the inlet passes through the adsorbent bed on its way to the second valve 702, more nitrogen may be adsorbed. In general, this second phase 720 of the cycle begins after the upper pressure is reached (i.e., at the end of the pressurization phase) and can last for any suitable time. For example, it can be advantageous for the second phase 720 to continue for as long as the average purity of the product gas 703 is above a certain level (e.g., that meets pipeline standards and/or corresponds to a methane content of at least 95%) and/or the average pressure of the product gas 703 is above a certain level (e.g., at or above pipeline pressure). In certain embodiments, the second phase continues for as long as the product gas withdrawn 703 from the adsorbent bed meets pipeline standards and/or is above a predetermined pressure (e.g., pipeline pressure). Depending on the pipeline, pipeline pressure may be above about 35 atm to about 70 atm, or higher (e.g., pipeline pressure can be about 40 atm absolute (573 psig or 4053 kPa)).

While some of the product gas 703 may be used within the process (e.g., as a purge or repressurization gas), one advantage of this PSA cycle is that it can provide product gas that can be injected into a natural gas distribution system (e.g., natural gas grid) and/or liquified, with substantially no or reduced compression costs. Accordingly, it can be advantageous to provide substantially all of the gas withdrawn during the second phase 720 for injection into the natural gas distribution system and/or for liquefaction. In certain embodiments, at least a portion of the product gas 703 is injected into a natural gas distribution system (e.g., natural gas grid), either directly, or after temporary storage (e.g., in a pipe or tank). In certain embodiments, at least a portion of the product gas 703 is liquified, either directly or after temporary storage (e.g., in a pipe or tank).

In certain embodiments, the depressurization in the second phase 720 includes multiple depressurization steps wherein the gas is withdrawn as aliquots having different average pressures. In such embodiments, each of the aliquots may be provided to a separate temporary storage (e.g., based on pressure), or some of the aliquots may be combined (e.g., in a pipe or tank) to provide a combined gas having a certain average pressure (e.g., suitable for injection into a natural gas distribution system with no or minimal compression). Some aliquots, or combined aliquots, may be injected into the natural gas distribution system without compression while other aliquots, or combined aliquots, may be compressed prior to injection. In embodiments that includes multiple depressurization steps, there may or may not be a disruption in the withdrawal of gas 703 from the adsorbent bed between successive depressurization steps.

Since the product gas 703 is only withdrawn during one or more depressurization steps (i.e., is not withdrawn when feed gas is being fed into the adsorbent bed), this PSA process is distinct from conventional PSA processes that include an adsorption step following a pressurization step (i.e., where feed gas is provided as product gas is withdrawn and where the pressure is substantially constant in the adsorbent bed as product gas is withdrawn). While the adsorption phase in conventional PSA cycles can be advantageous (e.g., for providing the product gas at a constant pressure), it has now been found that for the high pressures achievable with the instant disclosure and/or when the feed gas is provided as a plurality of pressurized gas feeds, that it can be more advantageous to provide the combination of the first phase and second phase discussed above. For example, it can increase the yield of purified gas.

In the third phase 730, which is a depressurization phase (i.e., a second depressurization phase), the adsorbent bed 700 is depressurized in one or more steps to provide withdrawn gas 704. This involves withdrawing gas from the adsorbent bed 700, typically through the first valve 701 and/or the second valve 702 (e.g., preferably from the second valve as shown in FIG. 6). In general, there may or may not be a disruption in the withdrawal of gas from the adsorbent bed 700 between the second 720 and third 730 phases. Rather, the second phase 720 can be distinguished from the third phase 730, in how the withdrawn gas is treated (or not treated). For example, gas can be continuously withdrawn from the second valve 702 throughout the second and third phases, and the transition between the second phase 720 to the third phase 730 can be defined by a switch in where the withdrawn gas is directed (e.g., from an injection system to a tank). In general, the gas withdrawn during the third phase 730 may be directed according to its purity, its pressure, properties of the cycle, and/or an intended use.

While at least some of the withdrawn gas 704 may be provided for use outside of the PSA cycle (e.g., to provide heat and/or power) and/or may be further purified (e.g., recycled within this PSA cycle, fed to another PSA cycle, or fed to another purification system), one advantage of this PSA cycle is that the gas withdrawn during the third phase 730 can be sufficiently pure and/or of sufficiently high pressure to be useful within the process (e.g., as a purge gas and/or repressurization gas). Accordingly, it can be advantageous to provide at least some of the gas withdrawn during the third phase 730 for use within the process (e.g., as a purge gas and/or repressurization gas). In certain embodiments, at least some or all of the withdrawn gas 704 is used within the process (e.g., as a purge gas and/or repressurization gas) either directly, or after temporary storage (e.g., in a pipe or tank). In certain embodiments, the depressurization in the third phase 730 includes multiple depressurization steps wherein the gas is withdrawn as aliquots having different average pressures. Such aliquots can be fed in order of increasing pressure to a single tank, or each of the aliquots can be provided to a separate tank. In certain other embodiments, the depressurization in the third phase 730 includes a single depressurization step wherein the gas is withdrawn and provided to a single tank.

In a fourth phase 740, which is a depressurization phase (i.e., a third depressurization phase), the adsorbent bed 700 is depressurized in one or more steps to provide withdrawn gas 705. This involves withdrawing gas from the adsorbent bed 700, typically through the first valve 701 and/or the second valve 702 (shown from the second, but could be the first). In general, there may or may not be a disruption in the withdrawal of gas between the third 730 and fourth 740 phases. For example, the third phase 730 can be distinguished from the fourth phase 740 in how the withdrawn gas is treated (or not treated).

In general, the gas withdrawn from the fourth phase 740 will have a higher nitrogen content than gas withdrawn in the third phase 730, but will still contain a significant amount of methane. Accordingly, it can be advantageous to further purify at least some of the withdrawn gas 705. While at least some of the withdrawn gas 705 may be provided for use outside of the PSA cycle (e.g., to provide heat and/or power) and/or provided to another PSA cycle or other purification system, the composition and relatively low pressure of the withdrawn gas 705 makes it particularly suitable for being recycled within this PSA cycle and/or fed to another PSA cycle. In certain embodiments, some or all of the withdrawn gas 705 is recycled by feeding it into an adsorbent bed (e.g., a regenerated bed) as part of the first phase of this cycle. In such embodiments, the withdrawn gas 705 is used, at least in part, as a repressurization gas. In certain embodiments, at least a portion of the withdrawn gas increases the pressure of an adsorbent bed in the first phase of the cycle to some intermediate pressure (e.g., from a relatively low pressure, which could be less than atmospheric, about atmospheric, or above atmospheric), and feed gas is provided to increase the pressure from the intermediate pressure to the upper pressure. Advantageously, recycling at least a portion of the withdrawn gas 705 allows the withdrawn gas 705 to be further purified and used to produce additional product gas at elevated pressures.

The fourth phase 740 of the cycle may continue until the adsorbent bed 700 is substantially depressurized (e.g., to about atmospheric pressure). For example, in certain embodiments, the adsorbent bed is be depressurized to about 10 atm, about 9 atm, about 8 atm, about 7 atm, about 6 atm, about 5 atm, about 4 atm, about 3 atm, about 2 atm, about 1 atm, or lower (e.g., 0.1 atm). Pressures provided in atm refer to the absolute values, unless otherwise stated. Depressurization of the adsorbent bed to about 1 atm can be advantageous in that it avoids using a vacuum while removing a significant amount of nitrogen from the adsorbent bed. Since at least some of the withdrawn gas 705 may be at a relatively low pressure (e.g., atmospheric), in certain embodiments, at least a portion of the withdrawn gas 705 is fed to a compressor and/or one or more tanks prior to being recycled. In certain embodiments, the depressurization in the fourth phase 740 includes multiple depressurization steps wherein the gas is withdrawn as aliquots having different average pressures. In such embodiments, each aliquot can be provided to a separate storage tank and/or adsorbent bed (if multiple adsorbent beds are used), with or without compression. In certain other embodiments, the depressurization in the fourth phase 740 includes a single depressurization step wherein the gas is withdrawn and provided to a single tank. Those skilled in the art will understand that the final pressure in this fourth phase may be determined in dependence upon whether there is a separate regeneration phase and/or its design. For example, if this depressurization is conducted down to 0.1 atm, a separate regeneration phase may not be required.

In a fifth phase 750, which is optional, the adsorbent bed 700 is regenerated. Although the final depressurization step can remove most of the gas within the adsorbent bed, and more specifically can reduce the pressure such that a majority of the nitrogen is desorbed by the end of the fourth phase, a significant amount of nitrogen and methane may still be present (e.g., within the void space), particularly if the final pressure in the fourth phase is about or greater than atmospheric. Providing one or more regeneration steps can remove this gas, and in particular can remove the nitrogen that otherwise could contaminate the methane product during the first phase of the next cycle. It may also improve methane recovery. Such regeneration steps, which are known in the art, can include evacuation (e.g., drawing a vacuum) and/or purging (e.g., with gas withdrawn in the second or third phases of the cycle). For example, purging the adsorbent bed can include passing a relatively pure methane stream counter-currently through the bed at low operating pressures such that the purge gas forces the more-strongly adsorbed nitrogen to be displaced from adsorption sites of the adsorbent material. While purge steps are often conducted at relatively low pressures (e.g., atmospheric), in some embodiments, elevated pressure(s) can be used for at least part of a purge step.

At least part of the gas withdrawn from the third phase and fourth phase of this cycle, and/or off gas from the fifth phase (e.g., purge gas) can be further purified and/or disposed of. For example, at least some of the withdrawn gas 704 and/or 705 may be further purified to produce additional product gas and/or process gas. This further purification, which can occur within this cycle or another cycle (e.g., of a second bed arranged in series), can produce an off gas that can be disposed of by feeding it to a flare or thermal oxidizer (e.g., to remove methane) prior to release to the environment. In certain embodiments, at least some of the withdrawn gas 704 and/or 705 is further purified using at least a second bed arranged in series with the first bed described above (e.g., via a second cycle). In certain embodiments, at least some of the withdrawn gas 704 and/or 705 is further purified using another technology.

Advantageously, this PSA cycle, which cycles between at least the first to the fourth phases, is particularly advantageous when feed gas is available at relatively high pressures and/or provided from a pressurized mobile vessel (e.g., a trailer). For example, while biogas transported by mobile vessel can have relatively high pressures (e.g., relative to a biogas grid), since the pressure typically decreases during decanting, it can be challenging to exploit this relatively high pressure. Providing a pressurization phase where no product gas is withdrawn, and where a significant number of adsorption sites are still open at the end of the phase, followed by a depressurization phase where product gas is withdrawn co-currently with respect to the feed direction, allows this relatively high pressure to be exploited, while also increasing the yield of purified gas.

Further advantageously, since at least a portion of the feed gas is available at relatively high pressures and/or since this PSA cycle facilitates the use of high pressure feeds, one or more gas ejectors, which operate by means of the Venturi effect and thus may be referred to as Venturi pumps, may be used. For example, in certain embodiments, relatively high pressure feed gas and/or process gas is fed to a Venturi pump where it is used as a motive gas to draw low pressure gas from one or more adsorbent beds (e.g., draw a vacuum). Accordingly, the process can be conducted with fewer moving parts (e.g., fewer vacuums and/or compressors), thereby reducing operating costs. Using a Venturi pump to withdraw gas from the adsorbent bed is particularly advantageous when the combined gas (e.g., that includes the high pressure motive gas and the low pressure gas from the adsorbent bed) is used for repressuring an adsorbent bed.

Those skilled in the art will understand that the properties of the cycles and/or equipment for the cycles described herein can be modified and/or used with alternate configurations and/or equivalents. Such properties can be dependent on each other and/or be selected in dependence on the specifics of the feed gas (e.g., composition), feed system (e.g., temporary storage tanks, flow rates, etc.), adsorbent bed (e.g., adsorbent, bed length, diameter, volume, position, orientation), and/or number of adsorbent beds. For example, while the filling/depressurization of the adsorbent bed is described with reference to opening and/or closing first and second valves, those skilled in the art will understand that this was for illustrative purposes. In practice, there may be one or more inlet valves and one or more outlet valves, connected to one or more manifolds. For purposes herein, reference to opening one end of the adsorbent bed (e.g., inlet/feed end or outlet/product end) refers to opening one or more valves so as to substantially allow gas to enter/exit the adsorbent bed from that end, while reference to closing one end of the adsorbent bed (e.g., inlet/feed end or outlet/product end) refers to closing one or more valves so as to substantially prevent gas from entering/exiting the adsorbent bed through that end. Those skilled in the art will also understand that while the adsorbent beds are illustrated as horizontal beds, in some embodiments, the adsorbent beds are vertically oriented. In this case, the feed gas can be provided from the top or bottom of the adsorbent beds. Providing feed gas from the top may reduce or obviate the risk of bed lifting during pressurization and/or may facilitate the use of higher velocities and/or quicker pressure equalizations.

With regard to the embodiment in FIG. 6, the timing of each phase can determine the purity and/or pressure of gas withdrawn during that phase and/or can affect certain properties of the cycle. For example, the third phase 730 (i.e., second depressurization) takes the adsorbent bed from a certain pressure (e.g., around pipeline pressure) to a lower pressure (e.g., above atmospheric). It can be advantageous to select this lower pressure such that it is sufficiently high enough to provide reasonably pure methane (e.g., greater than 92%, greater than 94%, greater than 95%, greater than 96% methane), while also being sufficiently low to generate enough flow to regenerate the media and/or be used as a process gas (e.g., for repressurizing this bed or another bed). In certain embodiments, the pressure of the adsorbent bed at the end of the third phase 730 is equal to or lower than about 37 atm (529 psig or 3749 kPa), is equal to or lower than about 35 atm (500 psig or 3546 kPa), is equal to or lower than about 30 atm (426 psig or 3040 kPa), or is equal to or lower than about 25 atm (352 psig or 2533 kPa). Alternatively, or additionally, the pressure of the adsorbent bed at the end of the third phase is higher than about 20 atm (279 psig or 2026 kPa). In certain embodiments, the pressure of the adsorbent bed at the end of the third phase 730 is between about 40% to about 60% of the upper pressure. Those skilled in the art will be able to readily select the appropriate conditions, including upper pressure, pressure boundaries for each phase, total duration of each cycle, duration of each phase, flow rates, etc., having the benefit of the teachings herein.

Gas Enriched in Methane

In general, at least a portion of the gas enriched in methane provided from the PSA process can be provided as product gas (e.g., upgraded biogas). For example, the PSA process may produce RNG that can be provided to a user and/or injected into a natural gas distribution system (e.g., the US natural gas grid). With regard to the latter, the RNG can be injected directly or transported (e.g., by truck, rail, or ship) to another location where it is injected.

In embodiments where the RNG is injected into a natural distribution system, the RNG may be at or above pipeline pressure for the injection. When the adsorbent for the PSA process is selective for one or more non-methane components (e.g., $N_2$), at least some of the gas enriched in methane may be provided at about the upper pressure. However, in embodiments where the gas enriched in methane is provided from a depressurization step, the product gas will be provided at decreasing pressures. In one embodiment, wherein gas enriched in methane is provided as part of a depressurization step, as the adsorbent bed depressurizes, the gas enriched in methane is provided to a plurality of storage tanks at a plurality of different pressures. For example, as the adsorbent bed is depressurized, a first portion of the gas enriched in methane is provided at a first average pressure $P_A$ to a first storage tank, a second portion of the gas enriched in methane is provided at a second average pressure $P_B$ to a second storage tank, a third portion of the gas enriched in methane is provided at a third average pressure $P_C$ to a third storage tank, etc., where $P_A > P_B > P_C$. The number of storage tanks may be dependent on the upper pressure of the adsorbent bed, the lower pressure of the adsorbent bed, and/or the desired pressure of the product gas. For example, the number of storage tanks may range from 2 to 20. Those skilled in the art will understand that such storage tanks are not limited to a particular shape or design and may be any suitable reservoir that can hold the various portions of pressurized product gas. For example, each storage tank may be a long and/or large diameter pipe section configured to hold the product gas. In providing different aliquots of the product gas at successively lower pressures, less of the product gas may require pressurization for pipeline injection. For example, only gas in the lowest pressure storage tanks may require compression. Alternatively, the product gas from the highest pressure tanks (e.g., above pipeline pressure) could be combined with gas from the lower pressure tanks, to provide a product gas a pressure close to pipeline pressure, thereby further reducing and/or obviating the compression requirements.

In one embodiment, a fuel credit or renewable energy credit associated with the RNG is generated or caused to be generated. The term "cause" or "causing", as used herein, refers to arranging or bringing about a specific result (e.g., a withdrawal of a gas from a distribution system), either directly or indirectly, or playing a role in a series of activities through commercial arrangements such as a written agreement, verbal agreement, or contract.

The term "credit", "renewable fuel credit", or "fuel credit", as used herein, refers to any rights, credits, revenues, offsets, greenhouse gas rights, or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract, or otherwise. The renewable fuel credit may be a certificate, record, serial number or guarantee, in any form, including electronic, which evidences production of a quantity of fuel meeting certain life cycle GHG emission reductions relative to a baseline (e.g., a gasoline baseline) set by a government authority.

The generation of fuel credits or renewable energy credits associated with the RNG may be related to the environmental attributes of the RNG and/or the corresponding life cycle GHG emissions. To determine life cycle GHG emissions associated with a fuel, analyses are conducted to calculate the GHG emissions related to the production and use of the fuel throughout its life cycle. Life cycle GHG emissions include the aggregate quantity of GHG emissions related to the full life cycle of the transportation fuel, including all stages of fuel and feedstock production and distribution, from feedstock generation or extraction, through the distribution and delivery, and use of the finished fuel to the ultimate consumer. GHG emissions typically account for total net GHG emissions, both direct and indirect, associated with feedstock production and distribution, the fuel production, and distribution and use.

In one embodiment, the RNG is provided for use as a transportation fuel and a fuel credit is generated or caused to be generated. Providing the RNG for transportation use is advantageous because fuel credits can be lucrative. Examples of fuel credits include, Renewable Identification Numbers (RINs) under the United States Environmental Protection Agency (EPA) Renewable Fuel Standard and carbon credits under state supported low carbon fuel standards within the United States (e.g., The Low Carbon Fuel Standard in California).

Advantageously, using the pressure from the transport of the feed facilitates a PSA process that operates at high upper pressures without compression from rotating parts. In addition to economic savings (e.g., operational and/or capital), reducing or obviating compression associated with the PSA process (e.g., including the product gas) may result in relatively low GHG emissions. Moreover, using the pressure from transport can facilitate the use of pressures that are higher than those required for efficient separation, and thus can improve the product recovery and/or purity provided by the PSA, particularly when based $N_2$ rejection.

Further advantageously, the instant disclosure can facilitate producing RNG from biogas produced from a plurality of sources (e.g., multiple landfills) via a centralized processing facility that provides PSA based $N_2$ rejection. While cryogenic $N_2$ rejection has generally been preferred for large scale $N_2$ rejection, it is not necessarily easy or economical to scale up once installed. The instant disclosure provides $N_2$ rejection that is modular and thus can be readily tailored (e.g., scaled up or down) to accommodate varying biogas supply. The method/system disclosed herein is particularly beneficial for use in centralize processing systems as it may be less expensive to incrementally expand in response to project growth.

For purposes herein, the term "enriched" means that the concentration of the corresponding component(s) has increased relative to its original or previous concentration (e.g., a gas enriched in methane has a higher methane content than the biogas fed into the adsorbent bed). In certain embodiments, the gas enriched in methane is comprised of from 90% to 99% methane.

Example 1

The following is an example of a PSA process designed for use with the feed preparation methods disclosed herein. While this PSA process has been designed for and is particularly beneficial for these feed preparation methods, it may be advantageous for any feed, including feed that is provided at a constant pressure. This example relies on calculations that assume the adsorbent is a $N_2$ selective Ba-ETS-4 and that the feed is 79% $CH_4$ and 21% $N_2$. The PSA process includes the following steps.

Step 1. Start. The adsorbent bed is initially in a regenerated state, at a pressure of about 0.1 atm absolute (1.46 psia or 10.1 kPa). At this low pressure, the concentration of bound $N_2$ is reasonably low.

Step 2. Feeding. The biogas is fed into an inlet at one end of the adsorbent bed, with the outlet at the other end closed. Feeding continues until the pressure increases to the upper pressure, which in this example is 250 atm (3660 psig or 25,330 kPa). During this step $N_2$ preferentially adsorbs on the adsorption material. More specifically, $N_2$ begins to adsorb onto the adsorption material as it enters the adsorbent bed, such that the concentration of adsorbed $N_2$ increases from the inlet end toward the outlet end, where the concentration of adsorbed $N_2$ is negligible. $CH_4$, which is less strongly adsorbed, passes through the adsorbent bed as the $N_2$ is adsorbed so that the gas near the outlet of the adsorbent bed is enriched in $CH_4$, and may have a methane purity of at least 99%. At this point, gas feeding stops.

Step 3. First decompression. With a valve at the inlet end closed, and feeding terminated, gas is withdrawn from the outlet end of the adsorbent bed. Since the gas at the outlet end has a relatively high purity (e.g., at least 99%) the gas initially withdrawn from the adsorbent bed can be provided as product gas. The pressure drops as product gas is withdrawn. Optionally, the product gas in collected in storage tanks at successively decreasing pressures (e.g., at 200 atm, 150 atm, 100 atm, 50 atm, and 1 atm). This minimizes or avoids the need to recompress product gas prior to use or prior to injection into a natural gas distribution system.

In general, the first decompression can reduce the pressure from the upper pressure 250 atm (3660 psig or 25,330 kPa) to any suitable lower pressure that is greater than about 1 atm. If the lower pressure is too low, an excessive amount of $N_2$ may end up in the product gas, thereby reducing product purity. If the lower pressure is too high an excessive amount of purified methane may remain in the adsorption column, thereby reducing methane recovery. Calculations suggest that a lower pressure that is in the range from about 4% to about 10% of the upper pressure when the upper pressure is greater than 50 atm, and in the range from about 10% to about 25% of the upper pressure when the upper pressure is below 50 atm, can provide a good compromise between product purity and product yield.

Step 4. Second decompression. Waste gas that is enriched in $N_2$ is withdrawn from the inlet end, while product gas enriched in methane continues to be withdrawn from the outlet end. This is carried out down to a pressure of about 1 atm.

In this step, the gas withdrawn from the inlet and outlet ends can be withdrawn using any suitable flow rates. If the product flow rate is too high (the waste flow rate is too low), an insufficient amount of $N_2$ will be removed from the adsorbent bed. If the product flow rate is too low (the waste flow rate is too high), there is a loss of yield of $CH_4$. Calculations indicate that one suitable approach is to adjust the flow rate of waste so that it is roughly double that of product until a pressure of about 3 atm is reached, at which time the flow rates are adjusted to be roughly equal.

Step 5. Regeneration of bed. A vacuum is drawn to remove addition $N_2$ from the adsorbent bed. For example, additional gas can be withdrawn from the adsorbent bed by passing a relatively high pressure gas through a Venturi pump also in fluid communication with the adsorbent bed such that lower pressure gas in the bed is withdrawn from the adsorbent bed as a result of the Venturi effect. For example, this vacuum can be achieved by closing the inlet end of the adsorbent bed, and providing a Venturi pump at the outlet end such that a pressurized feed at a relatively high pressure can be used to withdraw gas from the adsorbent bed at the product end, thereby achieving a vacuum within the adsorbent bed (e.g., 0.1 atm). The combined stream, which includes both feed and process gas, can be used to pressurize an adsorbent bed or can be disposed of or further treated. Alternatively, this vacuum can be achieved by closing the outlet end of the adsorbent bed, and providing a Venturi pump at the inlet end such that a waste gas having a relatively high pressure can be used to withdraw gas from the adsorbent bed at the product end, thereby achieving a vacuum within the adsorbent bed (e.g., 0.1 atm). Once the vacuum is achieved and held, the adsorbent bed is ready to return to Step 1 of the cycle.

This process is distinct from other PSA processes in that product gas is not withdrawn from the adsorbent bed until the inlet end of the adsorption is closed. Providing withdrawal of the target gas only after the upper pressure is reached advantageously allows the withdrawal of the product gas to be substantially independent of the pressurization process (e.g., which may be advantageous with the feed systems disclosed herein). Although the target gas is withdrawn only after the upper pressure is reached, the relatively high upper pressures achieved by using the pressure from transport (e.g., at least 1000 psi) allows more void space gas to be available during depressurization (e.g., more product gas is withdrawn) and increases the capacity of the adsorbent (e.g., more $N_2$ is bound), and thus may facilitate a relatively high system productivity or 2-3 fold higher than a conventional low-pressure system. Terminating the feed step well before saturation of the adsorbent bed allows the $N_2$ to continue to be adsorbed as the gas mixture passes through the adsorbent bed, thereby increasing product purity.

It has been shown, through calculations, that this PSA process can achieve a product purity greater than 99%, with product recovery of 97.3%, which is comparable to conventional PSA systems. In addition, it achieves a savings in capital and operating cost by avoiding recycle and recompression of off-gas (e.g., thereby improving productivity of the PSA process), facilitates the use of smaller adsorbent beds (e.g., as a result of improved productivity and/or relatively high pressures), and avoids relying on a mechanical vacuum pump (e.g., with moving parts). It is also more flexible than a conventional system utilizing more than 4 parallel adsorbent beds modeled after a Skarstrom-type PSA process, by using a modular design that is readily expanded.

Examples 2 and 3

The following are examples of PSA processes that may be used with the feed preparation methods disclosed herein. While these PSA processes have been designed for and are particularly beneficial for these feed preparation methods, they may be advantageous for any feed, including feed that is provided at a constant pressure.

These PSA processes were designed to upgrade biogas by separating methane and nitrogen (e.g., nitrogen rejection). While these PSA processes have been designed for and can be particularly beneficial for separating nitrogen and methane, they can also be useful for separating other gas mixtures. While these PSA processes can be used with feed gas having any composition, they are believed to be particularly useful when the feed gas has a methane content between about 70% and about 92%, a nitrogen content between about 8% and about 30%, and an oxygen and/or carbon dioxide content between about 0% and about 2%.

Figure 7A:
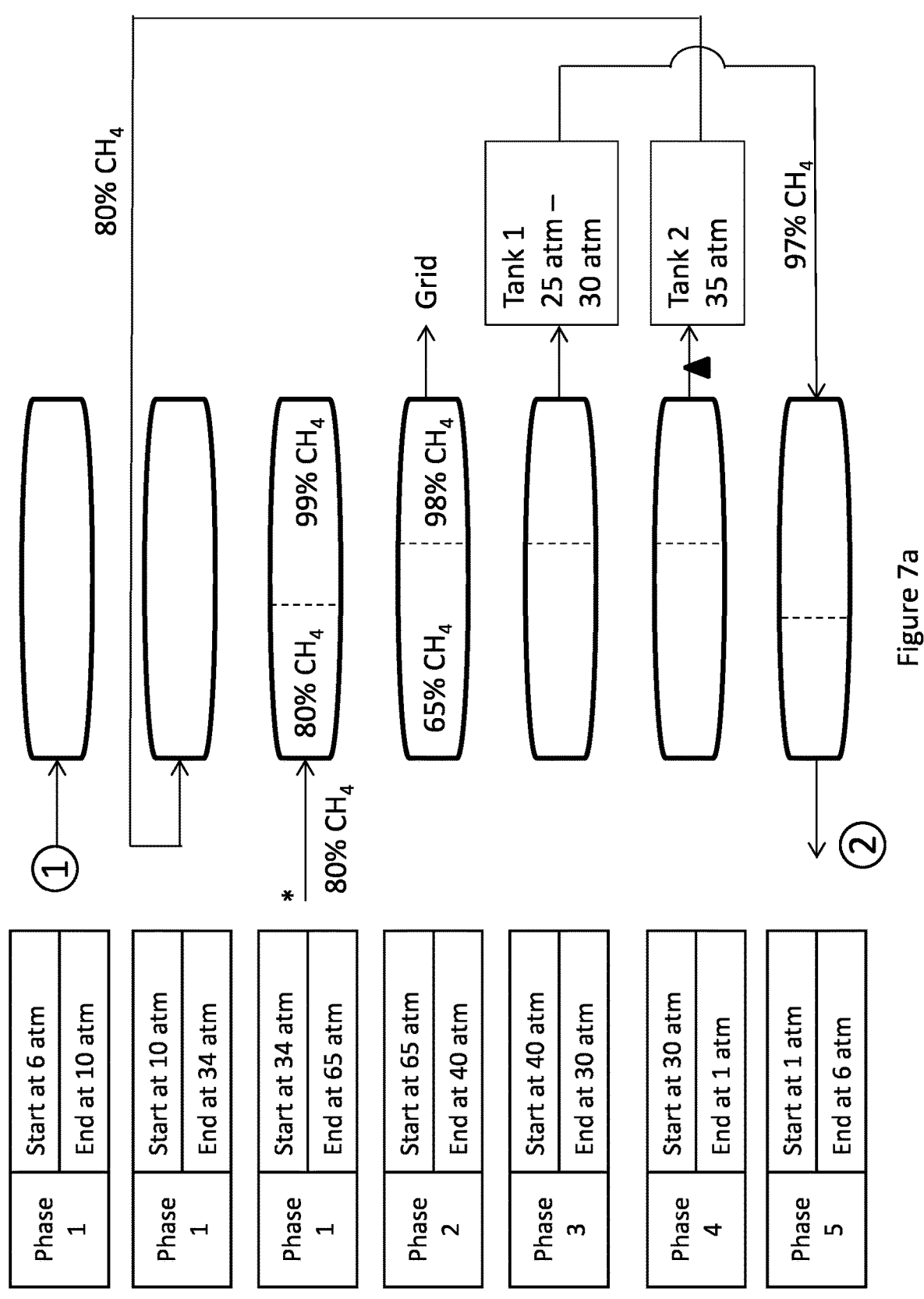
FIG. 7*a* is a schematic diagram showing an embodiment of a PSA cycle for a first adsorbent bed, which is in series with a second adsorbent bed.

Example 2 is discussed with reference to FIGS. 7a and 7b. Example 3 is discussed with references to FIGS. 8a and 8b. The PSA processes in each of these examples uses two beds in series, each of which contains an $N_2$ selective adsorbent such as $N_2$ selective Ba-ETS-4. The cycles for the first bed are described with reference to FIG. 7a and FIG. 8a (e.g., based on the PSA cycle described with reference to FIG. 6). The cycles for the second bed are described with reference to FIGS. 7b and 8b. For illustrative purposes each of the cycles is described with reference to a single adsorbent bed in the corresponding figure (e.g., FIG. 7a shows a single adsorbent bed in different phases of the cycle), however, those skilled in the art will understand that each of the PSA cycles can use multiple beds in parallel (not shown). For example, rather than simply cycling one adsorbent bed through the different phases, it can be advantageous to provided feed gas to multiple parallel adsorbent beds such that at least some of the parallel adsorbent beds can be in different phases and/or at different steps. The use of multiple, parallel adsorbent beds allows a continuous feed to be maintained. For example, if feeding comprises one-half of a cycle, then one bed is fed while the other depressurizes, then vice-versa once feeding the first bed is complete. The use of adsorbent beds in series may also improve the process. A first adsorbent bed is disposed in series with a second adsorbent bed when at least a portion of gas withdrawn from the first adsorbent bed is eventually routed to the second adsorbent bed (e.g., via a manifold, by opening and/or closing the appropriate values), where the second adsorbent bed is subjected to a different PSA cycle.

The properties of these PSA cycles, including the starting and final pressures of each phase, were modeled. In general, at the beginning of an adsorption phase, a mass transfer zone forms and moves through the bed. Nearly all of the adsorption occurs within this zone. For example, the concentration of the adsorbed species (e.g., nitrogen) decreases from its concentration in the feed gas to a very low value over the length of this zone. This zone can have a constant length (e.g., smaller than the overall length of adsorbent bed) and can move through the bed at a constant speed. Breakthrough of the adsorbed species from the adsorbent bed generally occurs when the front of the zone reaches the product end of adsorbent bed. The model used to determine the properties of the PSA cycles in FIGS. 7a, 7b, 8a, 8b assumes that the interface between the mass transfer zone and the rest of the bed has a negligible length. Such mass transfer zone is illustrated with a dashed line in the figures and would be the case if mass transfer occurred instantly. As this is not the actual case, the dashed line represents a useful idealization. For purposes herein, the area to the left of the mass transfer zone in FIG. 7a is referred to as the nitrogen adsorbed zone, whereas the area to the right of the mass transfer zone is referred to as Zone 2. The mass transfer zones in the figures, which correspond to the mass transfer zones at the end of the phase/step being depicted, is shown for illustrative purposes and does not necessarily correspond to the exact reality.

In each of the examples shown in FIGS. 7a,b and 8a,b, respectively, the model assumes that the feed gas provided for purification has a nitrogen content of 20% and a methane content of 80%, both on a volumetric or molar basis. Prior to feeding the biogas into the PSA cycle of the first bed it may be at any suitable elevated pressure. For example, in certain embodiments, the feed gas is provided at a pressure between about 65 atm to about 250 atm (about 940 psig to about 3674 psig, or about 6,560 kPa to 25,330 kPa). Such pressures are much higher than typically provided from a landfill or anaerobic digester, but can be achieved when biogas is compressed for storage and/or transport (e.g., to a centralized biogas upgrading facility) after partial purification (e.g., where carbon dioxide is removed). Such biogas may be at a temperature between about −20° C. and 60° C.

Referring to FIG. 7a, the PSA cycle for the first adsorbent bed in Example 2 includes five phases.

In the first phase, the adsorbent bed is pressurized to an upper pressure, which in this case is about 65 atm (about 940 psig or about 6586 kPa), but could be up to about 250 atm (about 3660 psig or about 25,331 kPa). The pressurization is conducted over three steps, each of which includes feeding feed gas or process gas into the adsorbent bed at one end of the adsorbent bed while the other end is closed. For discussion purposes, these ends are referred to herein as the feed end and the product end, respectively, although gas may pass therethrough in any direction. The valves for opening and/or closing the adsorbent beds, which can be control valves, are not shown. The feed gas (i.e., biogas containing 80% methane and 20% nitrogen) is fed into the feed end of the adsorbent bed in the third step (shown at *), after the adsorbent bed has been pressurized to about 34 atm (about 485 psig or about 3445 kPa) as described below. Feeding continues, with the product end closed, until the pressure increases to the upper pressure (65 atm). As the feed gas is fed into the adsorbent bed, nitrogen preferentially adsorbs on the adsorbent media over methane, starting at the feed end. As the feeding continues, the mass transfer zone moves through the adsorbent bed. In this example, the adsorbent bed is configured such the adsorbent bed is not saturated with nitrogen at the end of the first phase of the cycle. Rather the mass transfer zone is located near the middle of the adsorbent bed or towards the feed end (e.g., at about 32% of the length of the bed). The nitrogen adsorbed zone (i.e., where nitrogen is substantially bound/adsorbed to the adsorbent material) has a methane content of about 80%. Zone 2, which is still capable of adsorbing nitrogen, has a methane content in excess of 98%.

In the second phase, the adsorbent bed is depressurized from about 65 atm to about 40 atm (about 573 psig or about 4053 kPa), which may facilitate injection into certain natural gas pipelines without compression. More specifically, gas is withdrawn from the adsorbent bed from the product end. This results in the pressure within the adsorbent bed dropping and the mass transfer zone moving towards the product end. The first portion of gas withdrawn from the adsorbent bed will be the purest. As more gas is withdrawn from the bed, the methane purity may decrease (e.g., as more nitrogen is eventually withdrawn). At the end of the second phase the methane content in the $N_2$ adsorb zone is about 65%, while the methane content in Zone 2 is about 98%.

In this example, the PSA cycle for the first bed is designed such that all of gas being withdrawn in the second phase has a purity (e.g., greater than 98%) and pressure (e.g., greater than 40 atm) that facilitates injection into a natural gas distribution system with little to no additional compression. However, if the methane purity is not sufficient to meet pipeline specifications when the final pressure is 40 atm, the pressure at the end of this second phase can be selected to be higher (e.g., 50 atm), albeit at the cost of a lower throughput. Alternatively, if the methane purity would meet pipeline standards at pressures lower than 40 atm, then the pressure at the end of this second phase can be selected to be lower (e.g., 35 or 37 atm), and the pressure of the product gas can be increased to pipeline pressure by compressing at least a portion of it and/or by combining it with higher pressure product gas.

In the third phase, the adsorbent bed is depressurized from about 40 atm to about 30 atm (about 426 psig or about 3040 kPa). More specifically, gas is withdrawn from the adsorbent bed from the product end, yielding a withdrawn gas that is almost as enriched in methane as the product gas (e.g., about 97% methane). The withdrawn gas is used for regenerating the adsorbent bed in the fifth phase of the cycle and/or for use in the second bed cycle. Optionally, the withdrawn gas is first provided to a tank for temporary storage (e.g., Tank 1). The pressure of this tank may vary between about 25 atm (about 352 psig or 2533 kPa) and 30 atm as gas is withdrawn for use in regenerating the adsorbent bed in the fifth phase of the cycle. Advantageously, the choice of the pressure at the end of the third phase may be selected to be sufficiently high to provide a relatively high methane content (e.g., 97%), and sufficiently low to provide enough gas for regenerating the adsorbent bed in the fifth phase of the cycle and/or for use in the second bed cycle. In this example, the final pressure is 30 atm, however, other suitable pressures may include about 20 atm, about 25 atm, about 35 atm, about 37 atm, about 40 atm, or any pressures therebetween (e.g., between about 20 atm and about 40 atm).

In the fourth phase, the adsorbent bed is depressurized from about 30 atm to about atmospheric pressure. More specifically, gas is withdrawn from the adsorbent bed from the product end, and the withdrawn gas is recycled for use in an adsorbent bed in the first phase of the cycle. In this example, the withdrawn gas is compressed and fed to a second tank (e.g., at about 35 atm), before being used as a repressurization gas in the second step of the first phase of the cycle (e.g., pressuring the adsorbent bed from 10 atm to 34 atm). Alternatively, in order to avoid compressions costs, the gas withdrawn in the fourth phase can be withdrawn in aliquots having different average pressures (e.g., 25 atm, 15 atm, 10 atm) and fed into the second tank, or directly into an adsorbent bed in the first phase of the cycle, in order of increasing average pressures. Optionally, high pressure feed gas is provided to increase the flow rate and/or pressure (e.g., in the second tank). For example, in certain embodiments, high pressure feed gas is used as motive fluid for a gas ejector to draw out gas from the adsorbent bed when the pressure therein is relatively low (e.g., close to atmospheric). The resulting combined gas (i.e., the relatively high pressure feed gas used as a motive fluid and the relatively low gas withdrawn from the adsorbent bed), can be used to repressurize an adsorbent bed in the first phase of the cycle. This minimizes or avoids the need to recompress recycle gas.

In this example, the depressurization in the fourth phase continues to about atmospheric pressure. While choosing a pressure at the end of the fourth phase that is close to atmospheric can avoid the use of conventional vacuums and/or remove a significant amount of nitrogen, it is also possible for this pressure to be lower or higher than atmospheric. If this pressure is selected to be higher than atmospheric, the cycle may potentially be shortened, but there may be increased risk of more nitrogen being carried forward (e.g., reducing methane purity of the product). In certain embodiments, the pressure at the start and/or end of this phase is selected such that the average methane content of the withdrawn gas is substantially similar to that of the feed gas.

In the fifth phase of the cycle, the bed is regenerated (e.g., as gas withdrawn during the third phase of the cycle (e.g., and stored in tank 1) is fed into the adsorbent bed). More specifically, gas withdrawn in the third phase of the cycle (e.g., from the same or a different adsorbent bed) is fed into the product end of the adsorbent bed (i.e., gas is fed countercurrent relative to direction of feed gas provided in phase 1) until the pressure increases from about atmospheric to about 6 atm (about 74 psig or about 608 kPa). In this example, the feed end is closed during the repressurization, however, it is also possible for the feed end to be at least partially open (e.g., for all or some of this phase), thereby purging the adsorbent bed. Once the pressure reaches 6 atm, additional gas withdrawn in the third phase, is continuously passed though the adsorbent bed and fed to the second bed (e.g., at ②). At this point, the first adsorbent bed (the primary bed) is substantially stripped of nitrogen, is at a pressure of about 6 atm, and is ready to proceed to step 1 of the first phase of the cycle.

Figure 7B:
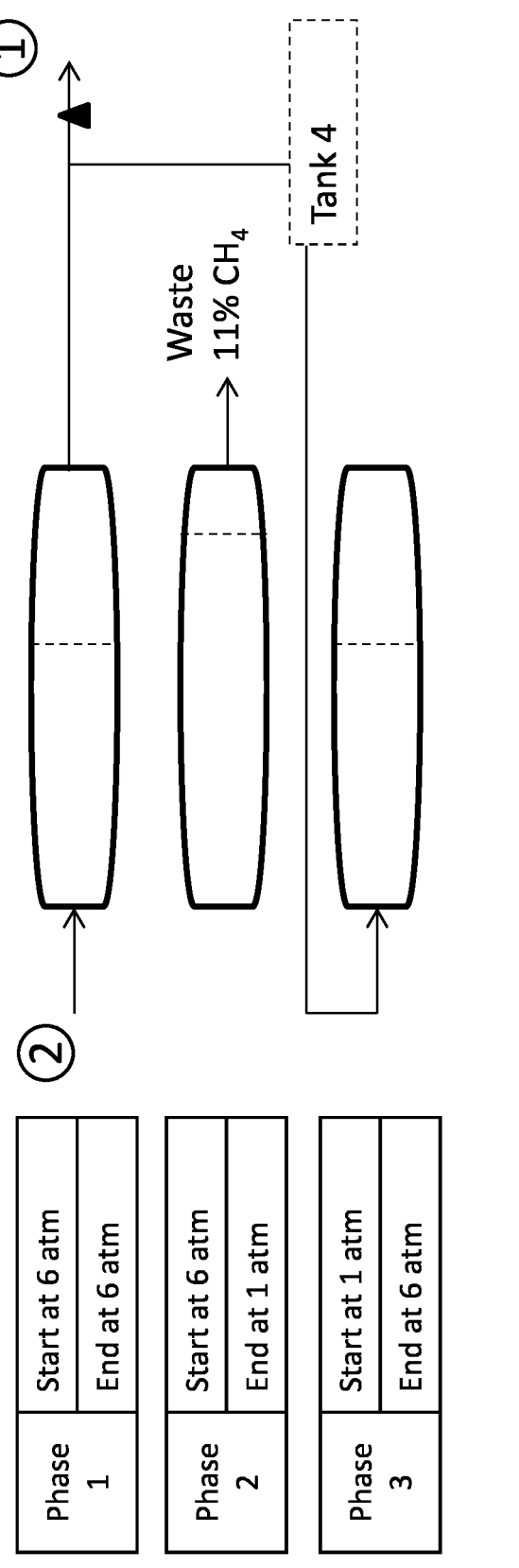
FIG. 7*b* is a schematic diagram showing an embodiment of a PSA cycle for the second adsorbent bed.

Referring to FIG. 7*b*, the PSA cycle for the second bed includes three phases.

In the first phase, which is an adsorption phase, the gas withdrawn from the first bed during the fifth regeneration phase is fed into the second bed (e.g., at ②). This gas, which may be provided directly (i.e., without temporary storage) or after temporary storage (not shown in FIG. 7b, but analogous to Tank 3 in FIG. 8b), is fed into the second bed when the second bed is at about 6 atm. As this gas is fed into the second adsorbent bed, nitrogen is adsorbed as the mass transfer zone moves through the second adsorbent bed, and a gas enriched in methane exits from the product end. This feeding continues until the second adsorbent bed is substantially saturated with nitrogen (e.g., before or after nitrogen breakthrough), and which time the feed end of the second bed is closed.

In this example, at least a portion of the gas enriched in methane withdrawn from the product end of the second bed is compressed to about 10 atm and used to pressurize an adsorbent bed in the first step of the first phase of the cycle in FIG. 7a (at ①). Another portion is used to repressurize the second adsorbent bed in the third phase of this cycle (see below). In this example, the portion used to repressurize the second bed in the third phase is first fed into Tank 4. However, configurations that do not use a tank for temporary storage may also be possible.

In the second phase, which is a depressurization phase, the gas within the second bed is withdrawn from the product end until the pressure reaches about 1 atm. This withdrawn gas, which has a methane content of about 11% can be subjected to further purification to increase methane recovery, or more likely can be treated as waste (e.g., flared or treated with a thermal oxidizer). In this example, the final pressure of 1 atm avoids the use of conventional vacuums and/or purge gas, however, it is also possible for the second bed to be subjected to a purge step or a vacuum.

In the third phase, the second bed is repressurized to about 6 atm using the gas enriched in methane from the first phase (e.g., from Tank 4). The repressurized second bed is ready to receive gas from the first bed.

Example 3, which is discussed with reference to FIGS. 8a,b, is similar to Example 2, but with some variation in, for example, the starting and ending pressures of some phases and/or in how the fifth phase is conducted.

In the first phase, the adsorbent bed is pressurized to about 72 atm (about 1044 psig or about 7295 kPa) in three steps. In each step, process gas or feed gas is fed into the adsorbent bed through the feed end, while the product end is closed. In the third step, feed gas is fed into the adsorbent bed (shown at *), after the adsorbent bed has been pressurized to 37 atm (about 529 psig or about 3749 kPa), and until the pressure reaches about 72 atm.

In the second phase, the adsorbent bed is depressurized from about 72 atm to about 40 atm (about 573 psig or about 4053 kPa). The resulting product gas, which is withdrawn from the product end, has a methane content of 98.8%. Methane recovery is 95.3%. This product gas, which has a pressure of at least 40 atm, is injected directly into a natural gas distribution system. Accordingly, the relatively high methane content and methane recovery can be achieved with significantly reduced compression costs.

In the third phase, the adsorbent bed is depressurized from about 40 atm to about 35 atm (about 500 psig or about 3546 kPa). More specifically, gas is withdrawn from the adsorbent bed from the product end, yielding a withdrawn gas that is almost as enriched in methane as the product gas (e.g., about 97% methane). The withdrawn gas is used for regenerating the adsorbent bed in the fifth phase of the cycle. In this example, the withdrawn gas is first provided to a tank for temporary storage (i.e., Tank 1). The pressure of this tank may vary between about 25 atm (about 353 psig or 2533 kPa) and 30 atm (about 426 psig or 3040 kPa).

In the fourth phase, the adsorbent bed is depressurized from about 35 atm to about 1 atm. More specifically, gas is withdrawn from the adsorbent bed from the product end, and the withdrawn gas is recycled for use in an adsorbent bed in the first phase of the cycle. In this example, the withdrawn gas is compressed and fed to a second tank (e.g., Tank 2 at about 40 atm), before being used as a repressurization gas in the second step of the first phase of the cycle, where it is used for pressuring the adsorbent bed from 5 atm to 37 atm.

In the fifth phase of the cycle, the bed is regenerated. More specifically, gas withdrawn during the third phase of the cycle (i.e., and stored in tank 1) is passed through the adsorbent bed in a counter current direction and with the bed at a pressure of about 1 atm while the feed end and product end are both open (e.g., the corresponding valves are at least partially open). At this point, the adsorbent bed is substantially stripped of nitrogen, is at a pressure of about 1 atm, and is ready to proceed to step 1 of the first phase of the cycle.

The gas that passes through and exits the first adsorbent bed in the fifth phase has a methane content of about 35%. It is compressed and fed to Tank 3, which is at about 6 atm (about 74 psig or about 608 kPa), and which is used to feed the second bed.

Figure 8A:
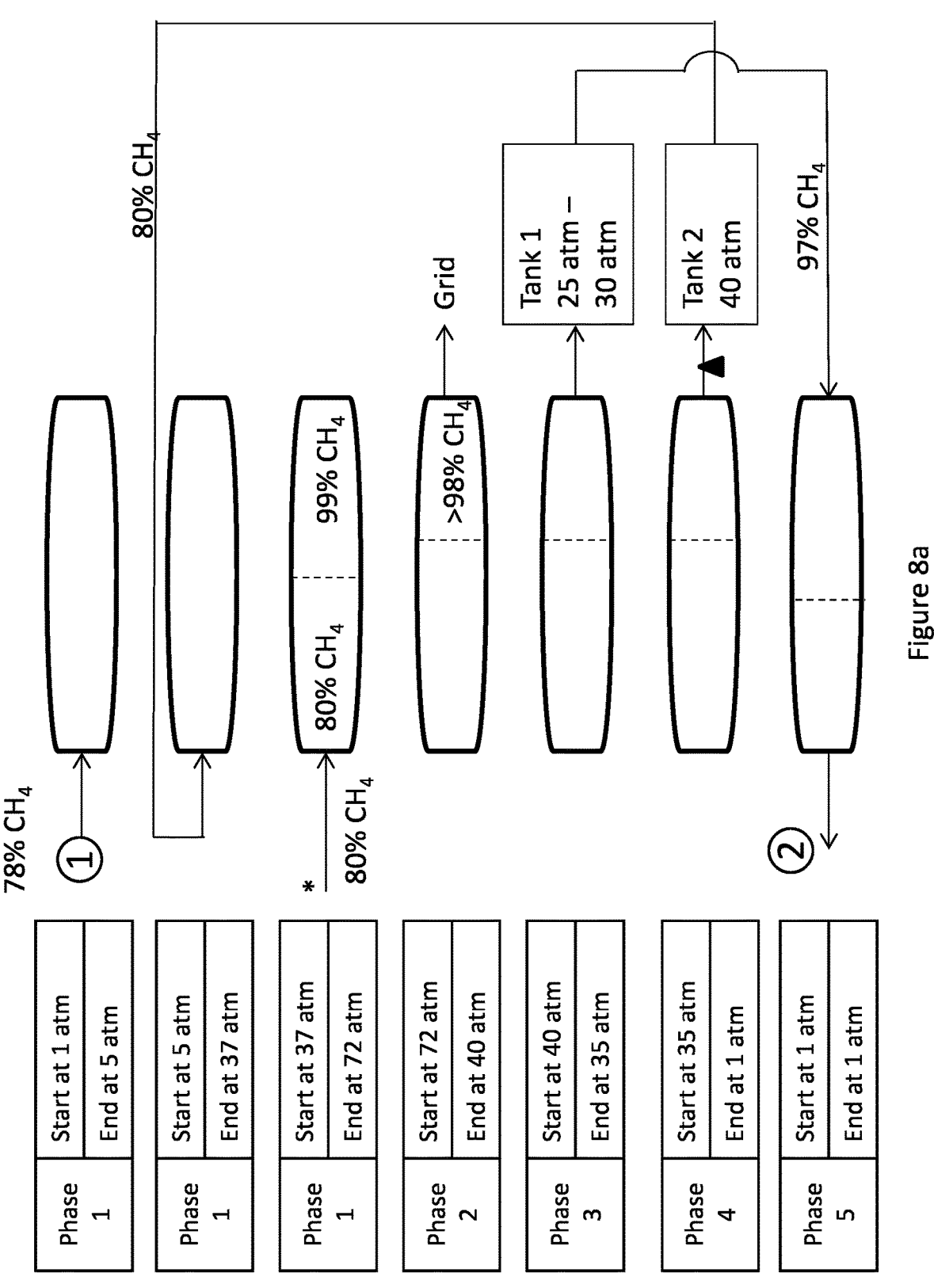
FIG. 8*a* is a schematic diagram showing another embodiment of a PSA cycle for a first adsorbent bed, which is in series with a second adsorbent bed.
Figure 8B:
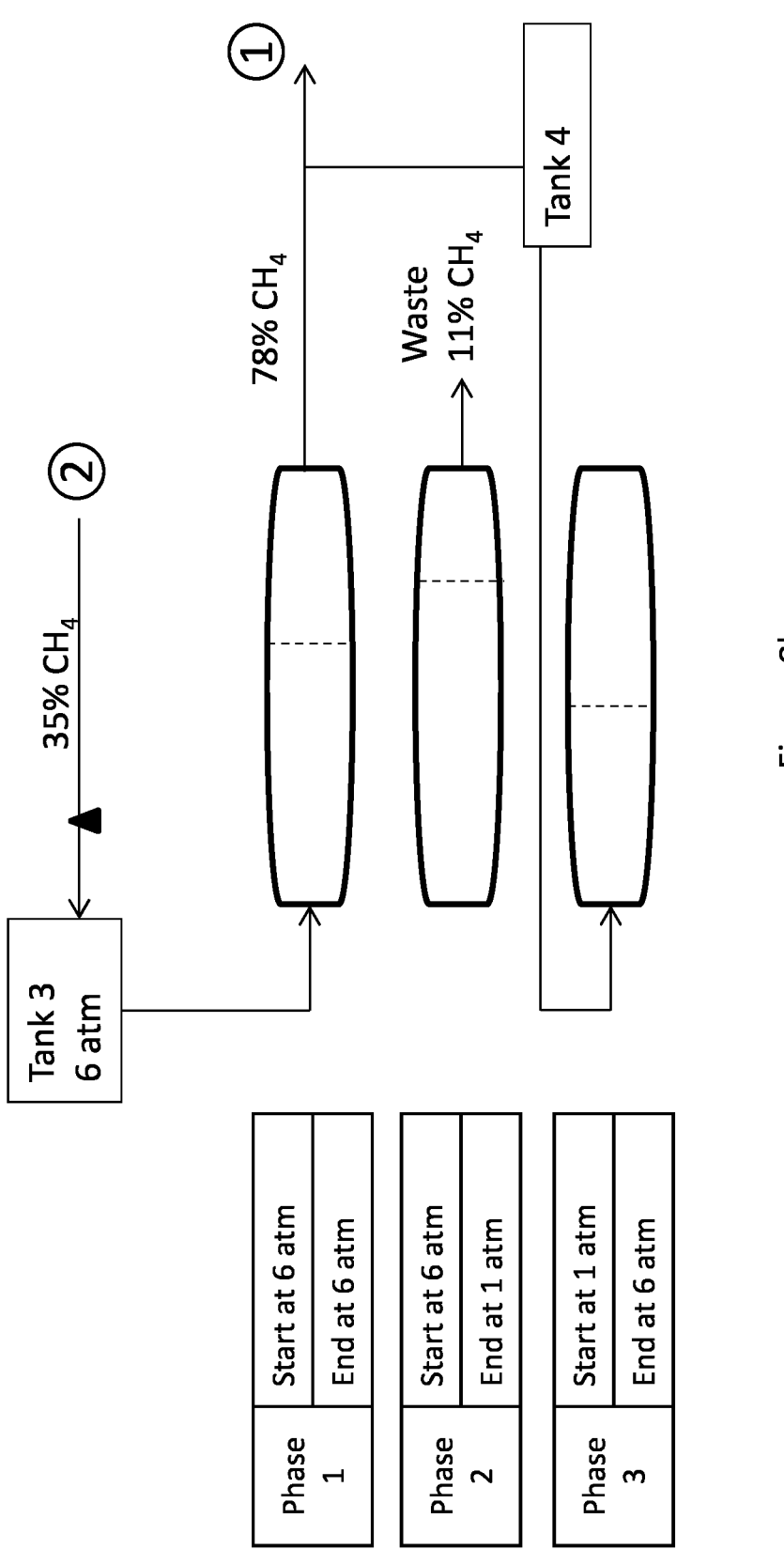
FIG. 8*b* is a schematic diagram showing an embodiment of a PSA cycle for the second adsorbent bed.

Referring to FIG. 8b, the cycle of the second bed includes a first phase, which is an adsorption phase. At the start of this first phase, the second bed is filled with relatively pure methane at about 6 atm. As the gas from Tank 3 passes through the second adsorbent bed the mass transfer zone also moves therethrough and nitrogen is adsorbed. At least a portion of the gas withdrawn during this phase is fed to step 1 of phase 1 of the first adsorbent bed (i.e., to pressurize the first bed to 5 atm). Another portion is used to repressurize the second adsorbent bed in Phase 3.

In the second phase, which is a depressurization phase, the second bed is depressurized. The depressurized gas, which has a methane content of about 11% may be treated as waste (e.g., be flared). The nitrogen recovery is about 89%

In the third phase, the second bed is repressurized using a portion of the gas withdrawn in the first phase.

In FIGS. 8a, 8b, compressors are provided to increase the pressure of the recycled gases. However, in certain embodiments, at least one of these compressors is replaced with a gas ejector.

Advantageously, such PSA cycles can exploit the nature of biogas transported in one or more vessels by vehicle. For example, they can exploit the relatively high pressure of such biogas so as to avoid relatively expensive vacuum systems and/or expensive recompression systems. In addition, such PSA cycles can work particularly well with the potentially intermittent delivery of biogas. For example, in certain embodiments, the biogas is delivered using one or more trailers at about 245 atm (3587 psig), each of which contains about 378,270 scf or 8.04 t of biogas (e.g., 80% $CH_4$, 20% $N_2$). Such biogas can be delivered at a rate of about one load per 1.2 hours. The PSA of some cycles herein (e.g., FIGS. 7a, 7b and 8a, 8b) can be configured to be timed in dependence of the delivery schedule and/or can be provided as needed. In certain embodiments, the first adsorbent bed is about 1/6 to about 1/4 the volume of a trailer (e.g., about 1/5 the size of a trailer). In certain embodiments, one or more of the trailers has a volume between about 44 m³ and about 46 m³, and the first adsorbent bed has volume of about 5 m³, about 6 m³, about 7 m³, about 8 m³, about 9 m³, about 10 m³, or about 11 m³. In certain embodiments, the number of adsorbent beds provided for the cycles in FIGS. 7a and/or 8a (e.g., first beds), is selected in dependent on the number of bays available for accommodating trailers. For example, in certain embodiments, there are twice as many beds as there are bays. In certain embodiments, there are 6 adsorbent beds provided; four in use, and two in stand-by mode.

Yet another advantages of such PSA cycles is that the adsorbent beds can be relatively small and/or that the systems can be modular (e.g., readily expanded). For example, in the PSA system illustrated in FIGS. 8a/8b, the first bed had a volume of about 7.85 m³ (e.g., length of 10 m, diameter of 1 m), whereas the second bed had a volume of 3 m³. Although the adsorbent beds are relatively small, since additional compression is not required, the feed gas may be provided relatively quickly (e.g., relative to using a compressor). Assuming that the feed rate increased the pressure by 6.8 atm/min, the total cycle for the first bed was 10.2 minutes, with the first phase taking 5.1 minutes and the other phases also 5.1 minutes combined. The PSA process is able to process 5300 SCFM of feed gas in this cycle.

Further advantageously, such advantages, including reduced costs, can be achieved while providing product gas with a methane purity greater than 98%, while the methane recovery is greater than 95%. This high purity and methane recovery is comparable to that achieved using systems wherein the feed gas is at the operating pressure of an adsorption phase, but with large amounts of internal compression and high vacuum for regeneration of the adsorption media.

These impressive results, which were achieved using a model that assumes instant mass transfer have also been substantially replicated based on modelling using finite mass transfer.

Of course, the above embodiments have been provided as examples only. It will be appreciated by those of ordinary skill in the art that various modifications, alternate configurations, and/or equivalents will be employed without departing from the spirit and scope of the invention. For example, in FIGS. 8a, 8b, compressors are provided to increase the pressure of the recycled gases. However, in certain embodiments, at least one of these compressors is replaced with an ejector. For example, in certain embodiments, the fourth phase of this cycle includes withdrawing the gas from the product end until the pressure falls to some lower pressure (e.g., 10 atm), and then using the feed gas as a motive force to withdraw more gas (e.g., there may be some overlap between step 1 and step 2 of the first phase). Accordingly, the scope of the invention is therefore intended to be limited solely by the scope of the appended claims.

The invention claimed is:

1. A method of upgrading biogas comprising methane and nitrogen, the method comprising:

(i) providing the biogas in at least one pressurized vessel, the biogas provided at least initially at a pressure of at least 65 atm (6586 kPa);

(ii) treating at least a portion of the biogas in a pressure swing adsorption (PSA) process, the PSA process comprising feeding the portion of the biogas into a first adsorbent bed disposed in series with a second adsorbent bed, the first adsorbent bed having an inlet end and an outlet end, the first adsorbent bed comprising an adsorbent selective for nitrogen over methane and subjected to a first PSA cycle, the first PSA cycle comprising:

a) a feed phase, wherein the portion of the biogas is fed into the first adsorbent bed when the inlet end is open and the outlet end is closed, thereby pressurizing the first adsorbent bed to a first pressure and preferentially adsorbing the nitrogen over the methane, the first pressure being at least 40 atm (4053 kPa);

b) a first depressurization phase, wherein the inlet end is closed, the outlet end is open, and a gas enriched in methane is withdrawn through the outlet end as the pressure of the first adsorbent bed falls to a second pressure, the second pressure lower than the first pressure, at least a portion of the gas enriched in methane provided as product gas;

c) a methane recovery phase, wherein gas is withdrawn from the inlet end, outlet end, or a combination thereof, as the pressure of the first adsorbent bed falls to a third pressure, the third pressure being lower than the second pressure, at least a portion of the gas withdrawn from the first adsorbent bed during the methane recovery phase recycled for use in the feed phase, used in a regeneration phase, fed to the second bed, or any combination thereof; and, d) optionally, the regeneration phase, wherein the first adsorbent bed is depressurized to 1 atm (101 kPa) or lower, subjected to a purge step, or a combination thereof.

2. The method according to claim 1, wherein the methane recovery phase comprises a second depressurization from the second pressure to an intermediate pressure, and a third depressurization from the intermediate pressure to the third pressure, the intermediate pressure being higher than the third pressure.

3. The method according to claim 1, wherein the first pressure is at least 120 atm (12159 kPa).

4. The method according to claim 1, wherein the first pressure is at least 200 atm (20265 kPa).

5. The method according to claim 1, wherein the second pressure is at least 35 atm (3546 kPa).

6. The method according to claim 1, wherein the gas enriched in methane is injected into a natural gas distribution system without compression after being withdrawn from the first adsorbent bed.

7. The method according to claim 1, wherein the intermediate pressure is between 20 atm (2026 kPa) and 37 atm (3749 kPa).

8. The method according to claim 1, wherein the intermediate pressure is between 25 atm (2533 kPa) and 35 atm (3546 kPa).

9. The method according to claim 1, wherein at least a portion of gas withdrawn from the first adsorbent bed during the second depressurization is provided to the second bed.

10. The method according to claim 1, wherein the third pressure is at least 1 atm (101 kPa) and less than 15 atm (1520 kPa).

11. The method according to claim 1, wherein the third pressure is between 0.1 atm (10 kPa) and 5 atm (507 kPa).

12. The method according to claim 1, wherein at least a portion of the gas withdrawn from the first adsorbent bed during the third depressurization is recycled for use in the feed phase.

13. The method according to claim 1, wherein the second adsorbent bed is selective for methane over nitrogen.

14. The method according to claim 1, wherein the second adsorbent bed is selective for nitrogen over methane.

15. The method according to claim 1, wherein the first PSA cycle comprises the regeneration phase, and wherein the second bed is fed off gas from the regeneration phase.

16. The method according to claim 1, wherein the methane recovery phase comprises simultaneously withdrawing a first portion of the gas from the first adsorbent bed through the inlet end, and a second portion of the gas from the first adsorbent bed through the outlet end.

17. The method according to claim 16, wherein a flow rate of the first portion of gas withdrawn through the inlet end is initially higher than a flow rate of the second portion of gas withdrawn through the outlet end.

18. The method according to claim 17, wherein the flow rate of the first portion of gas withdrawn through the inlet end is substantially equal to the flow rate of the second portion of gas withdrawn through the outlet end after the first adsorbent bed falls to a pressure of about 3 atm.

19. The method according to claim 1, wherein the regeneration phase comprises evacuating the first adsorbent bed using a Venturi pump.

20. A method of upgrading biogas comprising methane and nitrogen, the method comprising:

(i) providing the biogas in at least one pressurized vessel, the biogas provided at least initially at a pressure of at least 65 atm (6586 kPa);

(ii) treating at least a portion of the biogas in a pressure swing adsorption (PSA) process, the PSA process comprising feeding the portion of the biogas into a first adsorbent bed disposed in series with a second adsorbent bed, the first adsorbent bed having an inlet end and an outlet end, the first adsorbent bed comprising an adsorbent selective for nitrogen over methane and subjected to a first PSA cycle, the first PSA cycle comprising:

a) a feed phase, wherein the first portion of the biogas is fed into the first adsorbent bed when the inlet end is open and the outlet end is closed, thereby pressurizing the first adsorbent bed to a first pressure and preferentially adsorbing the nitrogen over the methane, the first pressure at least 40 atm (4053 kPa);

b) a first depressurization phase, wherein the inlet end is closed, the outlet end is open, and a first gas enriched in methane is withdrawn through the outlet end as the pressure of the first adsorbent bed falls to a second pressure, the second pressure at least 34 atm (3447 kPa) and lower than the first pressure, at least a portion of the first gas enriched in methane provided as product gas;

c) a second depressurization phase, wherein the inlet end is closed, the outlet end is open, and a second gas enriched in methane is withdrawn through the outlet end as the pressure of the first adsorbent bed falls to a third pressure, the third pressure lower than the second pressure, at least a portion of the second gas enriched in methane used within the PSA process;

d) a third depressurization phase, wherein gas is withdrawn from the inlet end, the outlet end, or a combination thereof, as the pressure of the first adsorbent bed falls to a fourth pressure, the fourth pressure lower than the third pressure, at least a portion of the withdrawn gas recycled for use in the feed phase; and e) optionally, a regeneration phase, wherein the first adsorbent bed is depressurized to 1 atm (101 kPa) or lower, subjected to a purge step, or a combination thereof.

21. A method of upgrading biogas comprising methane and nitrogen, the method comprising:

(i) providing the biogas in at least one pressurized vessel, the biogas provided at least initially at a pressure of at least 65 atm (6586 kPa);

(ii) treating at least a portion of the biogas in a pressure swing adsorption (PSA) process, the PSA process comprising feeding the portion of the biogas into an adsorbent bed, the adsorbent bed having an inlet end and an outlet end, the adsorbent bed comprising an adsorbent selective for nitrogen over methane and subjected to a PSA cycle, the PSA cycle comprising:

a feed phase, wherein the portion of the biogas is fed into the adsorbent bed when the inlet end is open and the outlet end is closed, thereby pressurizing the adsorbent bed to a first pressure and preferentially adsorbing the nitrogen over the methane, the first pressure being at least 40 atm (4053 kPa);

a first depressurization phase, wherein the inlet end is closed, the outlet end is open, and a gas enriched in methane is withdrawn through the outlet end as the pressure of the adsorbent bed falls to a second pressure, the second pressure lower than the first pressure, at least a portion of the gas enriched in methane provided as product gas;

a methane recovery phase, wherein gas is withdrawn from the inlet end, outlet end, or a combination thereof, as the pressure of the adsorbent bed falls to a third pressure, the third pressure being lower than the second pressure, at least a portion of the gas withdrawn from the adsorbent bed during the methane recovery phase recycled for use in the feed phase, used in a regeneration phase, fed to another bed, or any combination thereof; and, optionally, the regeneration phase, wherein the adsorbent bed is depressurized to 1 atm (101 kPa) or lower, subjected to a purge step, or a combination thereof.

* * * * *